United States Patent [19]
Mushabac

[11] Patent Number: 5,343,391
[45] Date of Patent: Aug. 30, 1994

[54] DEVICE FOR OBTAINING THREE DIMENSIONAL CONTOUR DATA AND FOR OPERATING ON A PATIENT AND RELATED METHOD

[76] Inventor: David R. Mushabac, 919 Ocean Ave., Brooklyn, N.Y. 11226

[21] Appl. No.: 834,462

[22] Filed: Feb. 12, 1992

Related U.S. Application Data

[63] Continuation-in-part of Ser. No. 743,103, Aug. 9, 1991, Ser. No. 694,446, May 1, 1991, and Ser. No. 507,162, Apr. 10, 1990, said Ser. No. 743,103, is a continuation-in-part of Ser. No. 694,446, Apr. 10, 1990, and Ser. No. 507,162, Apr. 10, 1990, said Ser. No. 694,446, is a continuation-in-part of Ser. No. 507,162, Apr. 10, 1990.

[51] Int. Cl.⁵ .................................... G06F 15/00
[52] U.S. Cl. ................. 364/413.28; 433/72; 433/76; 433/79
[58] Field of Search ............ 433/72, 73, 74, 75, 433/76, 77, 78, 79, 80, 81, 108, 109; 364/413.28

[56] References Cited

U.S. PATENT DOCUMENTS

| | | | |
|---|---|---|---|
| 3,971,133 | 7/1976 | Mushabac | 32/2 |
| 4,182,312 | 1/1980 | Mushabac | 433/68 |
| 4,239,431 | 12/1980 | Davini | 414/1 |
| 4,344,755 | 8/1982 | Gold et al. | 433/76 |
| 4,349,277 | 9/1982 | Mundy et al. | 356/376 |
| 4,525,858 | 6/1985 | Cline et al. | 382/1 |
| 4,564,295 | 1/1986 | Halioua | 356/376 |
| 4,575,805 | 3/1986 | Moermann et al. | 364/474 |
| 4,577,968 | 3/1986 | Makosch | 356/356 |
| 4,610,630 | 9/1986 | Betush | 433/79 |
| 4,657,394 | 4/1987 | Halioua | 356/376 |
| 4,997,369 | 3/1991 | Shafir | 433/72 |

OTHER PUBLICATIONS

"Optical Methods to Measure Shape and Size" P. M. Boone *Adv. Dent. Res.* 1(1):27–38, Oct. 1987.
"Optical Methods to Measure Shape and Size" P. M. Boone (paper).

*Primary Examiner*—Roy N. Envall, Jr.
*Assistant Examiner*—Arim Bai
*Attorney, Agent, or Firm*—R. Neil Sudol; Henry D. Coleman

[57] ABSTRACT

A device for use in a dental or medical application to obtain three-dimensional contour information comprises a multiplicity of arm segments, first mounting elements for connecting the arm segments to one another to form an articulated assembly of the arm segments. A second mounting element serves to fix the articulated assembly relative to a person's head, while a third mounting element is provided for attaching a diagnostic or medical treatment instrument to the articulated assembly at a point spaced from the second mounting element. A feedback component or components are operatively coupled with at least some of the arm segments for providing electrical signal feedback data as to positions of the arm segments relative to one another, thereby providing information as to the position of the instrument relative to the person's head.

68 Claims, 20 Drawing Sheets

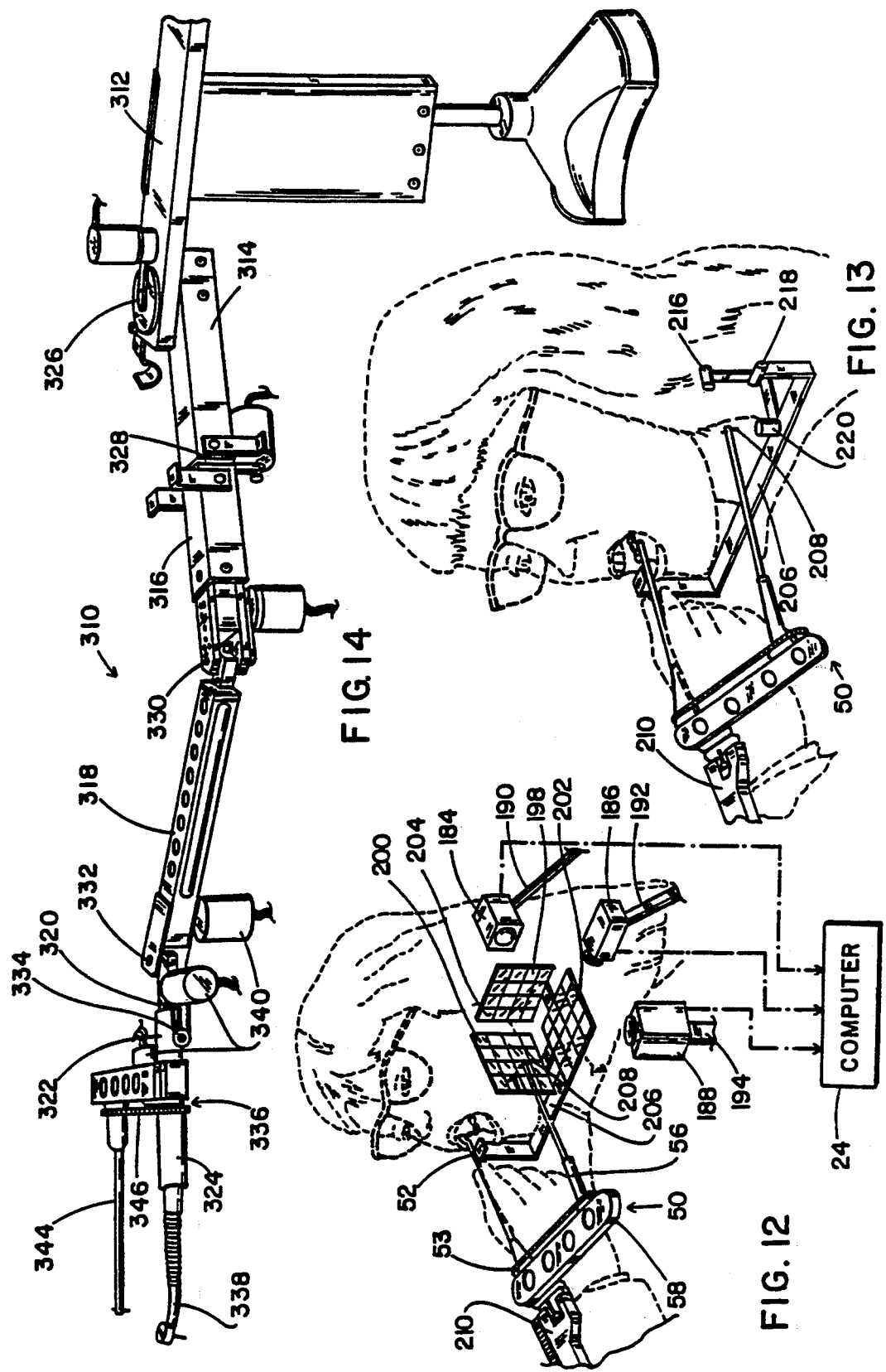

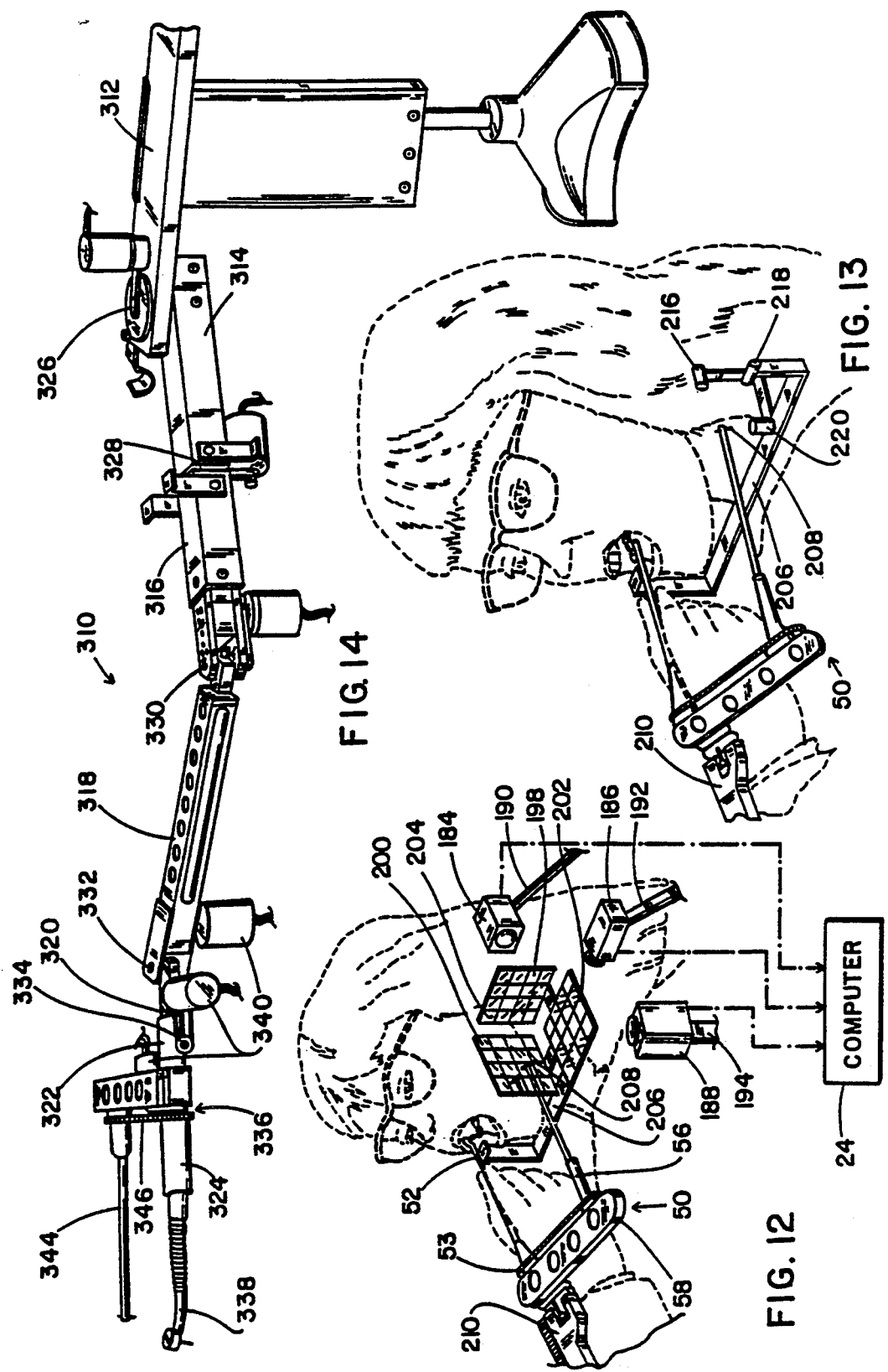

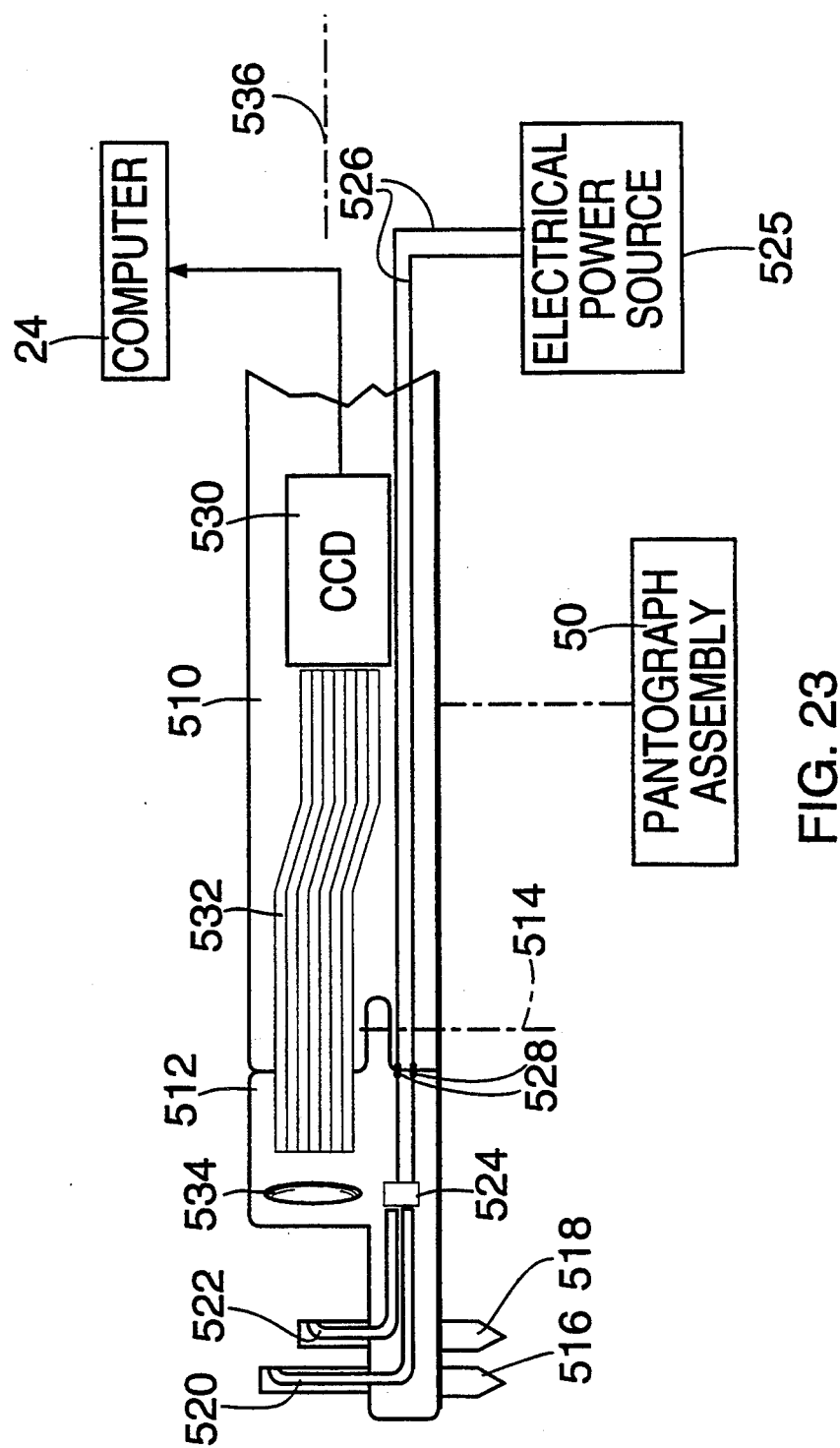

DEVICE FOR OBTAINING THREE DIMENSIONAL CONTOUR DATA AND FOR OPERATING ON A PATIENT AND RELATED METHOD

CROSS-REFERENCE TO RELATED APPLICATIONS

This application is a continuation-in-part of commonly owned U.S. patent application Ser. No. 743,103 filed Aug. 9, 1991, Ser. No. 694,446 filed May 1, 1991, and Ser. No. 507,162 filed Apr. 10, 1990. Application Ser. No. 743,103 is in turn a continuation-in-part of application Ser. No. 694,446 and application Ser. No. 507,162, while application Ser. No. 694,446 is a continuation-in-part of application Ser. No. 507,162.

FIELD OF THE INVENTION

This invention relates to a device for use in a dental or medical application to obtain three-dimensional contour information. This invention also relates to an associated device for use in operating on a patient. This invention further concerns a related method for use in a dental or medical application to operate on a patient or to obtain three-dimensional structural information as to a patient.

BACKGROUND OF THE INVENTION

U.S. patent application Ser. No. 507,162 discloses a system for modifying the shape of a three dimensional object such as a tooth in a patient's mouth. The system includes a pantograph type assembly for feeding to a computer digitized data representing surface contours of the tooth. The pantograph assembly includes a handheld probe inserted into the patient's mouth by a dentist. The dentist manipulates the probe so that a stylus tip of the instrument is held in contact with the tooth during tracing of a contour along the tooth. A pantograph extension outside the patient's mouth tracks the motion of the probe and particularly the stylus tip thereof, the motion of the pantograph extension being monitored by cameras which transmit video signals to the computer.

In an alternate embodiment of the contour data gathering device dislosed in application Ser. No. 507,162, an articulated arm assembly is fastened at a proximal end to a stationary fixture, while a distal end of the articular arm assembly carries a dental probe or drill. A plurality of digital encoders are operatively connected to the arms of the articulated assembly for providing respective electronic feedback signals which are fed to a computer. The computer uses the electronic feedback signals to calculate the position and orientation of the dental probe or drill.

In the articulated arm assembly, it has been observed that inaccuracies may creep into the computations of probe position and orientation. These inaccuracies are attributable in part to incremental flexures in the various arms of the articulated assembly and to changes in size owing to temperature effects.

The accuracy of the position and orientation computations is particularly important when the data is being used to calculate optimal locations and oreitnations of implant anchors or blades. Dental implants constitute a relatively recent development in dental practice and/or treatments. In an implant, the jaw bone of a patient is drilled to form a bore which receives a blade or anchor for an implant crown. To produce a desired and proper osseo integration and prosthetic and/or restorative placement of supra gingival restoration on the implant in its functional occlusal position, the dental practitioner or surgeon must precisely control the position, orientation and insertion of the blade or anchor. The ultimate position and orientation of the blade must take into account the thickness of the bone at the area of the implant, the proximity and orientation of adjacent teeth in the same jaw, and the location of teeth in the opposing jaw. In proper conventional implantation surgery, two or three people view the drill from different angles, to determine that the drilling is at a proper angle and location. Even under these circumstances, it is difficult to control the drilling operation so that the position obtained and orientation of the implant blade is optimal or acceptable.

Prior application Ser. No. 743,103 discloses a method and apparatus for facilitating the optimal placement of dental implant anchors. However, as noted above, the accuracy of the procedure is limited to some extent by the the equipment.

OBJECTS OF THE INVENTION

An object of the present invention is to provide an improved device for obtaining three-dimensional contour data.

A more particular object of the present invention is to provide such a device for obtaining more accurate three-dimensional contour data pertaining to a patient's head and, more specifically, to the patient's dentition.

Another object of the present invention is to provide such a device which is relatively inexpensive to manufacture.

A further object of the present invention is to provide such a device which is easy to use.

Another, more particular, object of the present invention is to provide such a device which facilitates operations on a patient, particularly including but not limited to, operations on a patient's dental structures.

An additional object of the present invention is to provide a related method for obtaining three-dimensional contour data and an associated method for operating on a patient's head, and more particularly on a patient's teeth or jaw bones.

SUMMARY OF THE INVENTION

A device for use in a dental or medical application to obtain three-dimensional contour information comprises, in accordance with the present invention, a multiplicity of arm segments, first mounting elements for connecting the arm segments to one another to form an articulated assembly of the arm segments. A second mounting element serves to fix the articulated assembly relative to a person's head, while a third mounting element is provided for attaching a diagnostic or medical treatment instrument to the articulated assembly at a point spaced from the second mounting element. A feedback component or components are operatively coupled with at least some of the arm segments for providing electrical signal feedback data as to positions of the arm segments relative to one another, thereby providing information as to the position of the instrument relative to the person's head.

Pursuant to another feature of the present invention, the second mounting element takes the form of a bite block for mounting the articulated assembly to a jaw of the person. The bite block advantageously includes a reference such as a landmark structure for establishing a coordinate system origin relative to the bite block. The bite block is preferably formed from a plurality of stock pieces and a setting composition for fitting the stock pieces to the person's jaw.

According to another feature of the present invention, an additional feedback component or components are operatively connected to the bite block and to the patient's jaw for monitoring incremental motions of the bite block relative to the jaw. The additional feedback component or components may take the form of strain gauges. The information provided by the gauges increases the accuracy of the position feedback.

According to a further feature of the present invention, a drive is mounted to the articulated assembly and is operatively connected to the instrument for incrementally moving the instrument about a point determined by the configuration of the articulated assembly. That point preferably constitutes an operating tip of the instrument. Additionally, a fourth mounting element is provided for removably mounting the instrument drive to the articulated assembly, while a computer control is operatively linked to the drive for energizing the drive and operating the instrument.

The drive removably mounted to the articulated assembly enables an operator to automatically call up from a computer's memory a stored motion sequence either recorded previously by the operator or by a third party specialist. The motion of the instrument (e.g., dental drill) is therefore optimized, while the operator merely guides the instrument to the location where the operation is to be performed.

Pursuant to another feature of the present invention, the feedback components include a plurality of digital encoders, linear motion encoders, rotary encoders, and/or gyroscopic elements.

A device for use in operating on a patient comprises, in accordance with the present invention, a multiplicity of arm segments, first mounting elements for connecting the arm segments to one another to form an articulated assembly of the arm segments, a second mounting element for fixing the articulated assembly relative to a person's head, a third mounting element for attaching an operating instrument to the articulated assembly at a point spaced from the second mounting element, and a drive operatively coupled with at least some of the arm segments for controlling and modifying positions of the arm segments relative to one another, thereby determining the position and orientation of the instrument relative to the person's head.

According to another feature of the present invention, the operating device further comprises a computer control operatively linked to the drive for controlling the activation of the drive.

A feedback component or components are operatively coupled with at least some of the arm segments and with the computer control for providing thereto electrical signal feedback data as to positions of the arm segments relative to one another, thereby informing the computer control as to the position of the operating instrument relative to the person's head.

A method for use in a dental or medical application to operate on a patient comprises, in accordance with the present invention, the steps of (a) attaching an articulated arm assembly to the patient's head, (b) automatically moving individual arms of the arm assembly to control position and orientation of an operating instrument attached to the assembly, and (c) automatically activating the instrument upon juxtaposition of an operating tip thereof with the patient.

The step of attaching the articulated arm assembly to the patient's head preferably includes the steps of fastening a bite block to the patient's jaw and mounting the arm assembly to the bite block. More preferably, the the bite block is formed from stock elements. Alternatively, the bite block may be automatically machined in a numerical control type procedure controlled by a computer in accordance with digitized three dimensional contour data on the patient's dentition. The three dimensional contour data is gathered by an optical input and/or by a dental probe with camera tracking of a pantographic slave probe and/or by an articulated arm assembly with encoder feedback, as described in detail hereinafter with reference to the drawings. In the last case, the articulated arm assembly may be attached at a base to a stationary fixture or may be mounted temporarily to the patient's jaw.

A method for use in a dental or medical application to obtain three-dimensional structural information as to a patient comprises, in accordance with the present invention, the steps of (i) attaching an articulated arm assembly to the patient's head, (ii) manually moving a probe instrument attached to the arm assembly so that a tracer tip of the instrument contacts a surface of the patient, (iii) automatically monitoring positions of individual arms of the arm assembly relative to each other during motion of the probe instrument, and (iv) automatically calculating in digital form the traced surface of the patient.

Pursuant to another feature of the present invention, the step of attaching the articulated arm assembly to the patient's head includes the steps of fastening a bite block to the patient's jaw and mounting the arm assembly to the bite block. The step of fastening includes the step of automatically machining at least one part of the bite block in accordance with electronic tooth surface data and may further include the step of automatically calculating an optimal point of attachment of the arm assembly to the bite block.

According to an additional feature of the present invention, incremental motions between the bite block and the patient's jaw are automatically monitored and taken into account in calculating the traced surface of the patient.

Pursuant to yet another feature of the present invention, the method further comprises the step of automatically moving the instrument in incremental motions about a point established by manually moving the instrument. Preferably, to automatically move the instrument, a drive device is temporarily attached to the arm assembly so that the instrument is operatively connected to the drive device; the drive device is then energized to move the instrument.

A device which is temporarily connected to a patient's jaw in accordance with the present invention obtains three-dimensional tooth and gum contour data which is significantly more accurate than data gathered via a device mounted to a stationary fixture. Accuracy is enhanced in part because the arms of an articulated assembly attached to a person's jaw are much shorter than arms mounted to a stationary fixture. The shorter arms are much less subject to flexural and thermal stresses. In addition, any inaccuracies in a long-arm assembly are proportionately magnified by the greater length of the arms.

Because a data gathering device mountable to a person's jaw is smaller than one mounted to a stationary fixture, it is less inexpensive to manufacture.

As set forth in U.S. patent application Ser. No. 507,162, it is necessary to monitor the patient's jaw to determine changes in the position and orientation thereof relative to the base of the articulated data-gathering assembly. Because these changes are apt to be substantial, the resulting error in determining tooth and gum contour surfaces is bound to be large as well. In contrast, in a data gathering device temporarily mounted to a patient's jaw, in accordance with the present invention, the base of the articulated arm assembly moves very little relative to the jaw. Accordingly, contour or surface computation error is reduced.

For similar reasons, a motorized drilling or shaping device in accordance with the present invention results in a more accurate cutting of a patient's dentition (teeth, bone).

The enhanced accuracy provided by the present invention has usefulness in all areas of dentistry, particularly including, but not limited to, implantology, periodontics, bridge and crown work and charting. In addition, the invention may be applied to medical surgery such as brain surgery where high accuracy is necessary.

A device in accorance with another embodiment of the present invention for use in a dental/medical application to obtain three-dimensional contour information comprises a hand held dental instrument, a plurality of first gyroscope components each capable of generating an electrical output signal indicative of orientation of the respective first gyroscope component and first mounting elements for mechanically connecting the first gyroscope components to the dental instrument to provide electrical output signals indicative of the orientation of the dental instrument. A plurality of second gyroscope components each capable of generating an electrical output signal indicative of orientation of the respective second gyroscope component are mechanically connect to a patient's jaw to provide electrical output signals indicative of the orientation of the jaw. A signal generator mechanically at least in part to the patient's jaw produces electrical output signals indicative of the translatory position of the dental instrument relative to the jaw, while a computer is operatively connected to the first gyroscope components, the second gyroscope components, and the signal generator for receiving the electrical output signals thereof and for computing the position and orientation of the dental instrument relation to the jaw.

A device for use in operating on a patient comprises, in accordance with one embodiment of the present invention, (i) an operating instrument, (ii) a hand-held carrier, the instrument being movably connected to the carrier, (iii) a drive assembly mounted to the carrier and operatively connected to the instrument for moving the instrument relative to the carrier, (iv) a tracking component operatively connected to the carrier for tracking the position and orientation thereof relative to a patient, and (v) a control unit operatively connected to the drive assembly and the tracking component for actuating the drive assembly to perform a predetermined operation on the patient partially in response to position and orientation of the carrier, as communicated to the control unit by the tracking component.

According to another feature of this embodiment of the present invention, the tracking component includes an articulated arm assembly and feedback means operatively coupled with the arm assembly and to the computer for providing thereto electrical signal feedback data as to positions of arm segments of the assembly relative to one another, thereby providing information as to the position of the carrier and the instrument relative to the patient.

Pursuant to another feature of the present invention, a locking component is operatively connected to the articulated arm assembly for temporarily locking the arm segments relative to one another to thereby fix the location of the carrier relative to the patient.

A device for use in a dental or medical application to track position and orientation of an instrument relative to a body part of a patient comprises, in accordance with another embodiment of the present invention, a reference element fixed to the body part of the patient, a first articulated arm assembly and a second articulated arm assembly. The first articulated arm assembly is connected to the reference element and to a stationary fixture, while the second articulated arm assembly is connected to the reference element and to the instrument. The first articulated arm assembly is provided with a first feedback mechanism and/or circuit for providing electrical signal feedback data as to position of and orientation of the reference element relative to the stationary fixture. The second articulated arm assembly is provided with a second feedback mechanism and/or circuit for providing electrical signal feedback data as to position of and orientation of the instrument relative to the reference element.

According to a more specific feature of the present invention, a drive assembly is mounted to the second articulated arm assembly and operatively connected to the instrument for automatically moving the instrument relative to the second articulated arm assembly. A locking mechanism may be operatively connected to the reference element and to the drive assembly for fixing the drive assembly relative to the reference element. More specifically, the locking mechanism is operatively connected to second articulated arm assembly for locking that assembly to establish a fixed position for the drive assembly relative to the reference element.

The body part to which the reference element is connected can be a person's jaw, the reference element taking the form of a bite block.

The feedback mechanisms and/or circuits are preferably connected to a common computer.

An alternative device for use in a dental or medical application to track position and orientation of an instrument relative to a body part of a patient comprises, in accordance with the present invention, (a) a reference element fixed to the body part of the patient, (b) a first articulated arm assembly connected to the reference element and to a first stationary fixture, and (c) a second articulated arm assembly connected to a second stationary fixture and to the instrumen. The first articulated arm assembly is provided with a first feedback mechanism and/or circuit for providing electrical signal feedback data as to position of and orientation of the reference element relative to the first stationary fixture, while the second articulated arm assembly is provided with a second feedback mechanism and/or circuit for providing electrical signal feedback data as to position of and orientation of the instrument relative to the second stationary fixture.

The position and orientation tracking device may further comprise a drive assembly mounted to the second articulated arm assembly and operatively connected to the instrument for automatically moving the instrument relative to the second articulated arm assembly. A locking mechanism may be operatively connected to the second stationary fixture and to the drive assembly for fixing the drive assembly relative to the second stationary fixture. More specifically, the lcoking mechansim may be connected to the second articulated arm assembly for locking that assembly to establish a fixed position for the drive assembly relative to the second stationary fixture.

The first stationary fixture and the second stationary fixture may be the same fixture or diffrnent fixtures spaced from one another.

A device for obtaining data as to position and orientation of a person's jaw comprises, in accordance with the present invention, a multiplicity of arm segments, a first mounting element or elements for connecting the arm segments to one another to form an articulated assembly of the arm segments, a second mounting element for fixing the articulared assembly to a stationary fixture, and a third mounting element for fixing the articulated assembly relative to a person's jaw. A feedback mechanism and/or circuit is operatively coupled with at least some of the arm segments for providing electrical signal feedback data as to positions of the arm segments relative to one another, thereby providing information as to the position of jaw relative to the stationary fixture.

A method for collecting three dimensional surface data comprises, in accordance with the present invention, the steps of (a) manually moving a probe instrument to define boundaries of structure, (b) electrically feeding, to a computer, data defining the boundaries, (c) upon the transmission of the data to the computer, manually holding another instrument for sensing three-dimensional surface data, and (d) automatically feeding, to the computer, surface data defining surfaces of the structure within the boundaries.

A method for use in modifying the shape of an object comprises, in accordance with the present invention, the steps of (1) digitizing surfaces of the object to generate an electronic model of the object, (2) operating a computer to modify the electronic model, (3) providing a physical model of the object, and (4) automatically controlling a tool to modify the physical model in accordance with the modification of the electronic model.

The tool and the instrument are advantageously connected to similar positioning and orientation devices, the step of automatically operating being similar to the step of automatically controlling. The positioning and orientation devices may each include an articulated arm assembly.

Pursuant to another feature of the present invention, this object modification method further comprises the step, per-formed subsequently to the step of automatically controlling, of automatically operating an instrument to modify the object in accordance with the modification of the physical model.

A method for executing a surgical operation comprises, in accordance with the present invention, the steps of (i) scanning internal structure in a patient, (ii) digitizing the internal structure in response to the step of scanning, and (iii) displaying an image of the internal structure in response to signals produced during the step of digitizing. Additional steps in the surgical method include (iv) providing a practice surgical instrument with a virtual operating tip, (v) moving the surgical instrument outside of the patient in a simulation of actual surgery on a portion of the internal structure, and (vi) automatically monitoring the instrument during the step of moving. Further steps are: (vii) displaying a representation of at least the operating tip of the instrument in overlap with the image of the internal structure during the step of moving, (viii) electronically recording motion of the surgical instrument during the step of moving, and (ix) automatically controlling an operating instrument to repeat the recorded motion of the surgical instrument.

The operating instrument may be used during the step of controlling to operate on the patient.

A surgical assembly comprises, in accordance with the present invention, a surgical tool, a manipulable member, and a motion reduction device operatively coupled to the manipulable member and the surgical tool for controlling motion of the tool to reproduce motions of the manipulable member on a reduced scale. The motion reduction device advantageously includes (i) a monitoring component operatively linked to the manipulable member for automatically detecting motions thereof, (ii) a computer operatively tied to the monitoring component for computing displacements on the reduced scale in response to signals from the monitoring component, and (iii) a motion control unit operatively connected to the computer and the surgical tool for moving the tool in accordance with signals from the computer. The monitoring component may include an articulated arm assembly connected to the manipulable member and may further include a feedback device or devices operatively connected to the articulated arm assembly for providing the computer with electrical signals coding successive positions and orientations of the manipulable member.

A device for performing a surgical operation comprises, in accordance with the present invention, a surgical instrument, a first drive operatively coupled to the instrument for incrementally moving the instrument about a reference point, a second drive operatively coupled to the instrument for shifting the reference point, and a detector operatively coupled to the instrument for monitoring position and orientation thereof. The detector preferably, but not necessarily, includes an articulated arm assembly and feedback device(s) operatively coupled with at least some arm segments of the articulated arm assembly for providing electrical signal feedback data as to positions of the arm segments relative to one another, thereby providing information as to position and orientation of the instrument. In one particular configuration, the articulated arm assembly is linked to a patient on whom the instrument is actuated to operate. For example, if the instrument is a dental instrument, the articulated arm assembly is attached to the patient's jaw, e.g., via a bite block. Alternatively, the articulated arm assembly may be linked to a stationary fixture, a sensor or group of sensors being operatively tied to the bite block for monitoring the position and orientation thereof relative to the stationary fixture. Preferably, a locking mechanism is operatively connected to the articulated assembly for temporarily locking the arm segments relative to one another to thereby fix the location of the reference point.

Pursuant to another feature of the present invention, the second drive may also include an articulated arm assembly and motors operatively coupled with at least some arm segments of the articulated arm assembly for driving the arm segments relative to one another, thereby shifting the reference point. An articulated linkage advantageously connects the articulated arm assembly of the second drive to the instrument, the assembly further comprising an additional locking mechanism operatively connected to the articulated linkage for temporarily locking individual links thereof relative to one another to firmly connect the articulated arm assembly of the second drive to the instrument.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

FIG. 12 is a partial perspective view, on an enlarged scale, of the contour generating device of FIG. 11, showing its use with a dental patient.

FIG. 13 is a partial perspective view, on an even larger scale, of another embodiment of the contour generating device of FIG. 1, showing its use with a dental patient.

FIG. 14 is a perspective view of another contour data generating device usable in a dentistry system.

FIG. 23 is a schematic side elevational view of yet another parallel contour data gathering device.

DETAILED DESCRIPTION OF THE INVENTION

Figure 1:
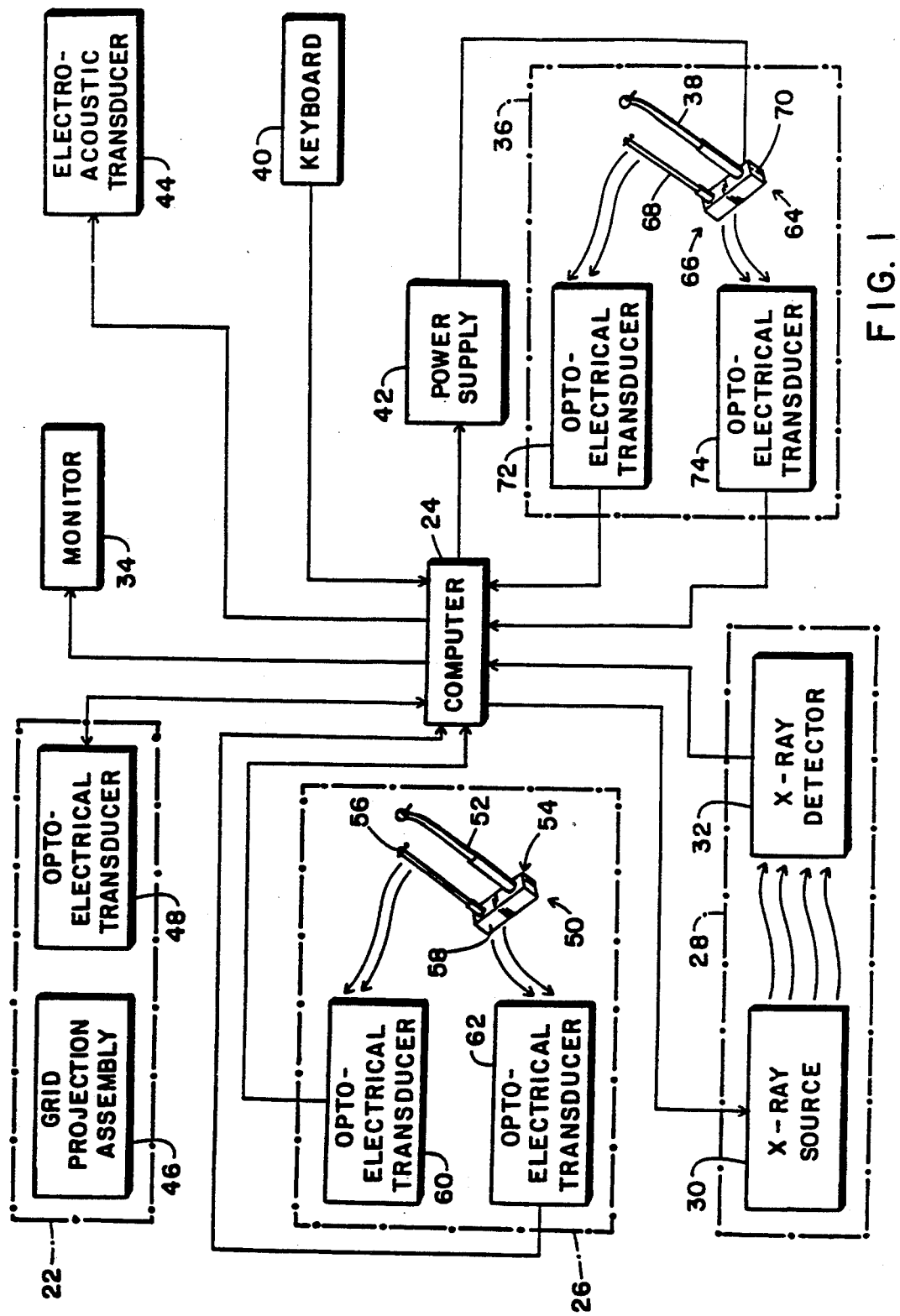
FIG. 1 is a block diagram of a system effecting a desired modification in the shape of a pre-existing object such as a tooth to which access is restricted.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a three-dimensional surface of an object such as a tooth. A second data generating device or assembly 26 is operatively connected to computer 24 for transmitting thereto digitized signals containing information pertaining to a curvilinear contour on the surface of the three-dimensional surface of the tooth. In addition, computer 24 may receive from a third data generating device or assembly 28 digitized input signals relating to internal structures of the tooth being scanned. Specifically, data generating device 28 may take the form of an X-ray device such as used in current extra-oral or intra-oral radiology or other methodologies and basically comprises a source 30 of X-ray radiation and a detector 32 for receiving the X-ray radiation after it passes through a tooth and converting the incident radiation into a digital data stream fed to computer 24.

As further illustrated in FIG. 1, the computerized interactive dentistry system also comprises a display device 34 such as a monitor or stereo or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized information that can be displayed on video as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth and to display such changes through its monitor or video connection.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or or to remove an outer layer of the tooth (in the case of preparing a form/shape for a crown or other prosthetic resotration). Computer 24 monitors the location of the operating tip of the drill via data generating device 36 and, if the drill approaches a boundary previously defined to the computer from prior programed parameters entered, for example, during an interactive tooth preparation selection operation, then signals are generated that display color changes of material removal information or interrupt the power provided to the drill via a supply 42 or alert the dentist via an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, it is to be appreciated that a grid may be imposed onto the tooth surface by other methods, such as adhesively attaching to the tooth surface a transparency provided with a grid.

As further depicted in FIG. 1 and described in detail hereinafter, data generating device 26 comprises a pantograph-type component 50 which incorporates a stylus handle or holding member 52 and a pantograph extension 54 in turn including a pantograph arm 56 and a bridge element 58. Bridge element 58 connects pantograph arm 56 to stylus holding member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" and forms a graphic model of the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26. The selection of the desired surface area may include outlined boundaries made directly on the patient's tooth with the probe unit. These outline boundaries may be combined with additional programed inputs that include a keyboard and/or a "mouse."

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

Data generating device 36 may be the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
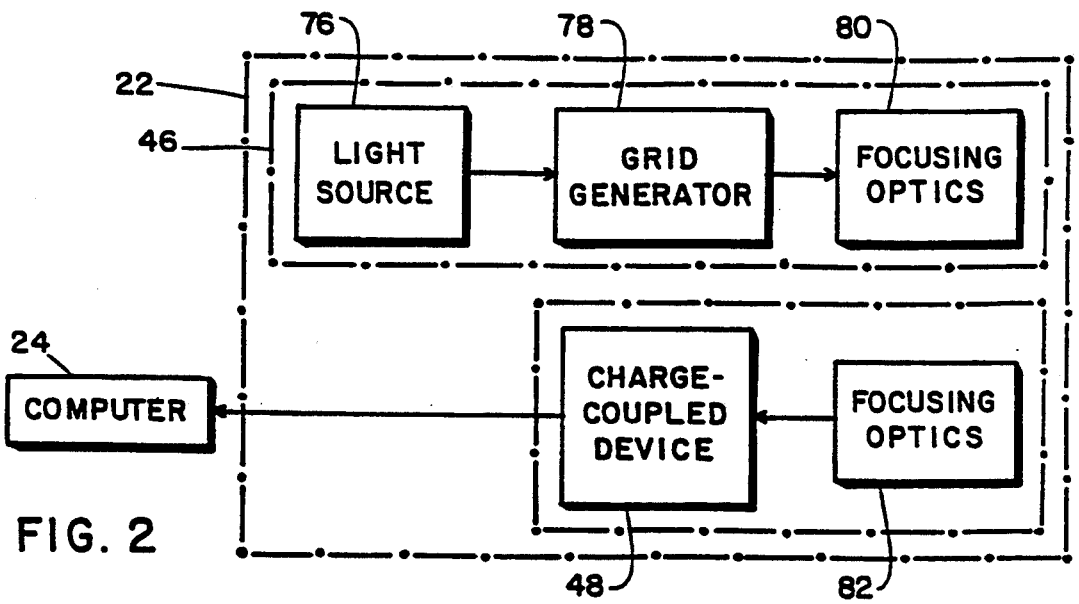
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figure 3:
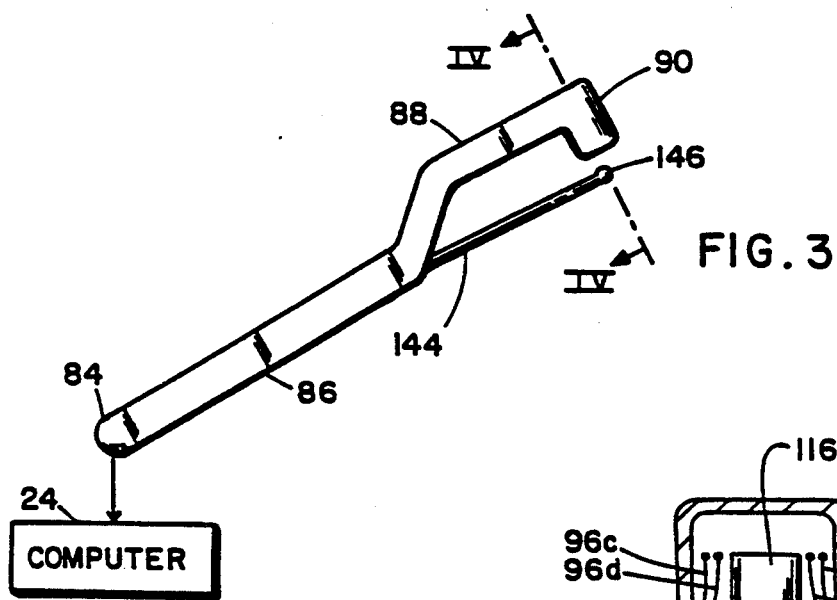
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
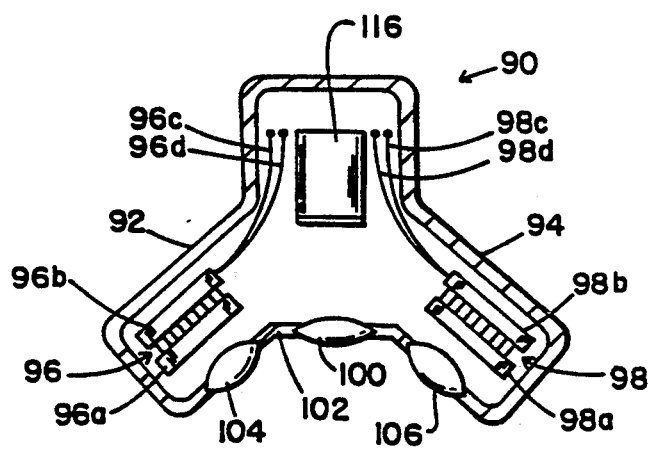
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitive sensor array 96a and 98b and respective sequencing and processing electronics 96b and 98b. The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
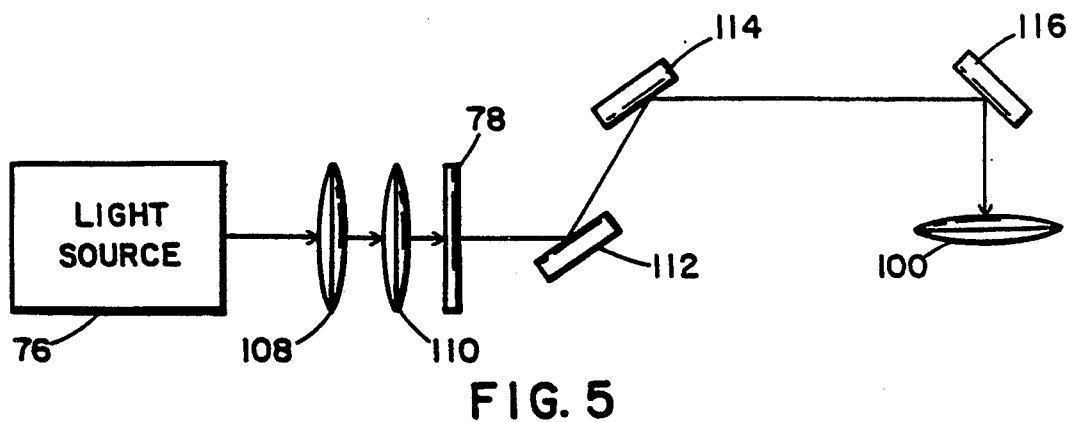
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
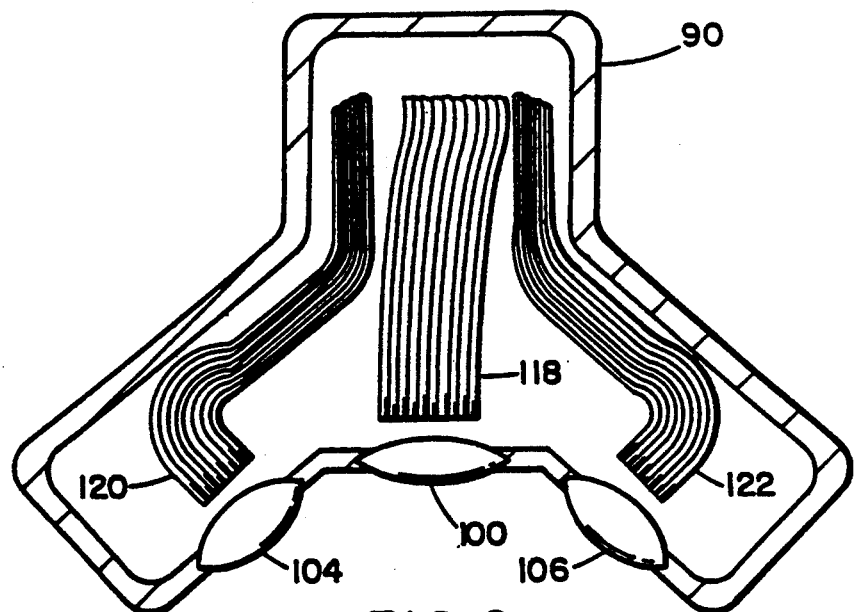
FIG. 6 is a cross-sectional view, similar to FIG. 4, of another particular embodiment of the surface data generating device of FIG. 2.

Grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
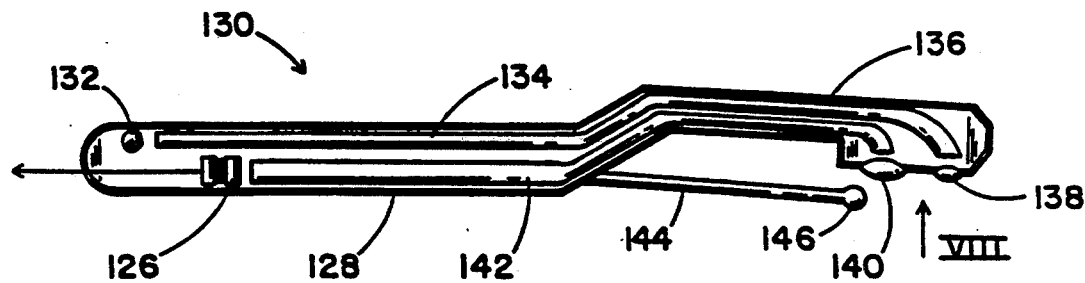
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels corresponding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

As depicted in FIGS. 11 and 12, contour data generating device 26 (FIG. 1) comprises three CCD cameras 184, 186 and 188 fixed to the free ends of respective adjustable mounting arms 190, 192 and 194 in turm connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 310 which extends from a fixed platform 312. Support arm 310 includes segments 314, 316, 318, 320, 322 and 324 of which the first segment 314 is connected to platform 312. Segments 314–324 are pivotably connected to one another via six rotating joints 326, 328, 330, 332, 334 and 336. By incorporating six separate junctions for rotational movement, an operating instrument (e.g., drill) 338 connected to the free end of a last or outermost arm 324 can move with six degrees of freedom, specifically along three translational axes and three rotational axes.

Stationary platform 312 and segment 314 are connected at joint 326 to provide rotation relative to one another about a substantially vertical axis. First segment 314 and second segment 316 are coupled to one another for rotation about an axis which is essentially a horizontal axis and which axis is coextensive with the axes of segments 314 and 316. Joint 28 provides this rotational movement. Similarly, arm segments 316 and 318 are rotatably linked via joint 330.

A probe or pantograph-type extension 344 is mounted to the outermost segment 324 and through a belt 346 rotates in synchronism with operating instrument 338. In this fashion, probe 344 is slaved to operating instrument 338. Accordingly, a three-dimensional configuration or contour traced by the tip of operating instrument 338 will be replicated by a tip of pantograph extension 344.

Each joint 326–336 is formed to have sufficient friction to allow the joint to hold a position once placed therein. However, the friction of each joint is low enough so that movement of the joint can be commenced fairly easily.

A plurality of digital encoders 340 are mounted to arm segments 314–324. Upon a movement of operating instrument 338, encoders 340 transmit to computer 24 respective signals encoding the amount of motion in the various six degrees of freedom. The monitoring device of FIG. 14 need not include pantograph extension 344 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 maybe provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputing dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In another structural procedure, a dentist and/or operator may use virtual preparation instruments to input specific percentages of tooth removal and to input specific boundaries and depths of tooth removal. The virtual preparation instruments include a telescopic stylus and/or drill substitutes. In yet another alternative procedure, computer 24 may be programed to recognize structural features of the tooth, such as its type, the location and shapes of cavities and prior inlays or onlays and to automatically select a possible preparation in accordance with the recognized features. The computer may be further programed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
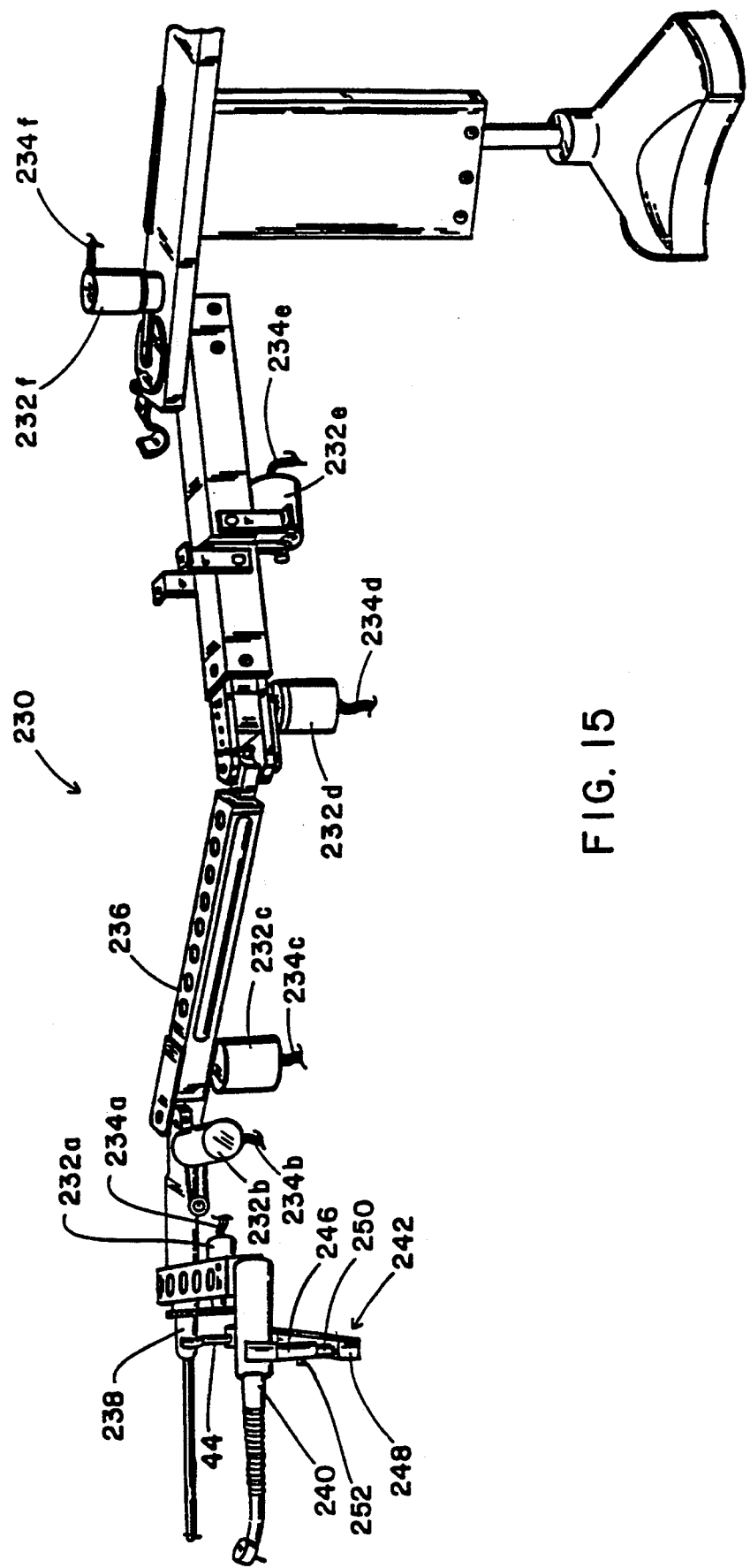
FIG. 15 is a perspective view of a drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a–232f connected via respective energization leads 234a–234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a–232f by computer 24 is not satisfactory to the dentist.

Upon the selection of a desired or optimum tooth preparation by a dentist and a subsequent signal for commencing tooth cutting, computer 24 generates a series of signals selectively energizing motors 232a–232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Limiting the motion of a dentist's drill 254 may be accomplished by selecting a tooth preparation preform 256 from a kit of preparation preforms. Preform 256 may be selected by computer 24, as described above, to confrom to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Figure 16:
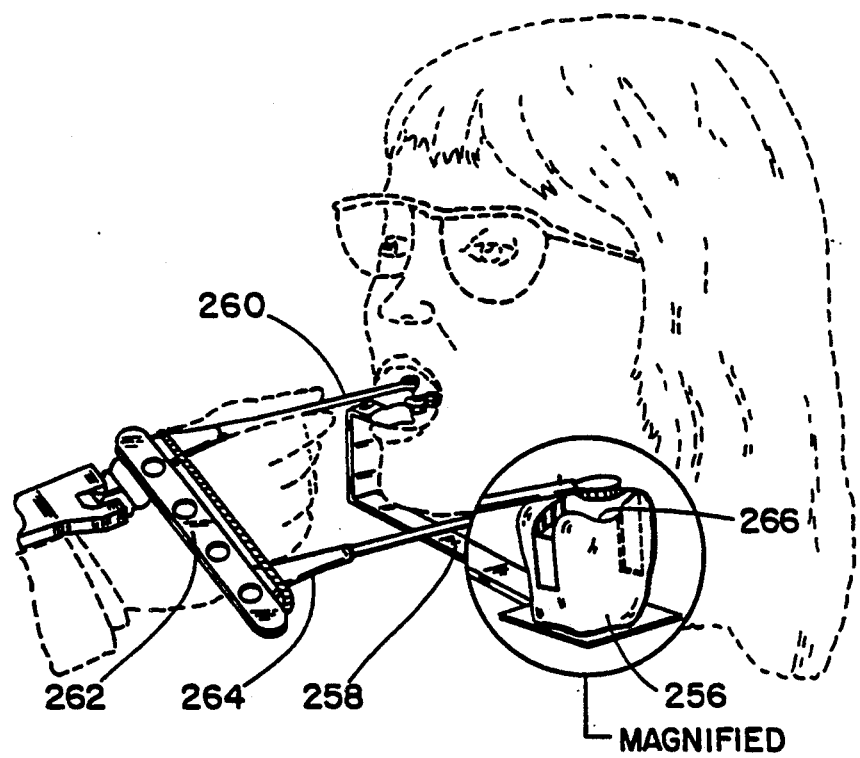
FIG. 16 is a partial perspective view, on an enlarged scale, of a drill movement restriction assembly, showing a tooth preparation preform on an even larger scale.

Accordingly, a kit is provided of dental preparation preforms in different sizes and shapes. Some preforms correspond to shapes of inlays such as that shown in FIG. 16. Other preforms correspond to shapes of onlays or crowns. The kit may also include prefabricated restorations or restorative devices, that is, preformed inlays and onlays for attachment and/or insertion to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective prosthetic or restorative inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay or crown. If necessary in a particular case, a selected preformed inlay or onlay or crown can be machined prior to attachment to a tooth. Computer 24 may control the machining operations in a conventional numerically con-trolled operation or may serve to limit the range of cutting motions, as described hereinabove with reference to providing a tooth with the desired preparation.

Figure 17:
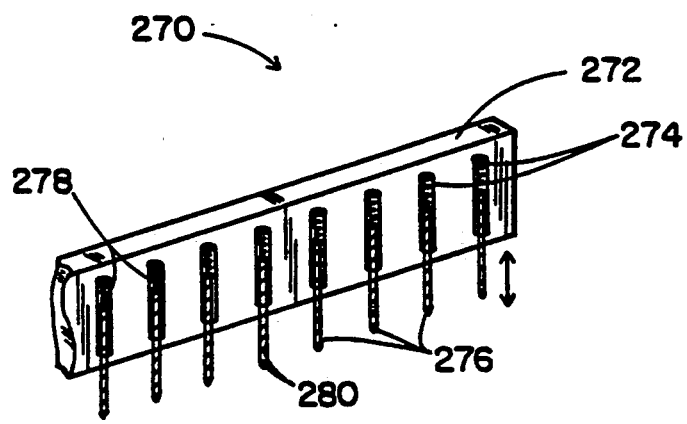
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Figure 18:
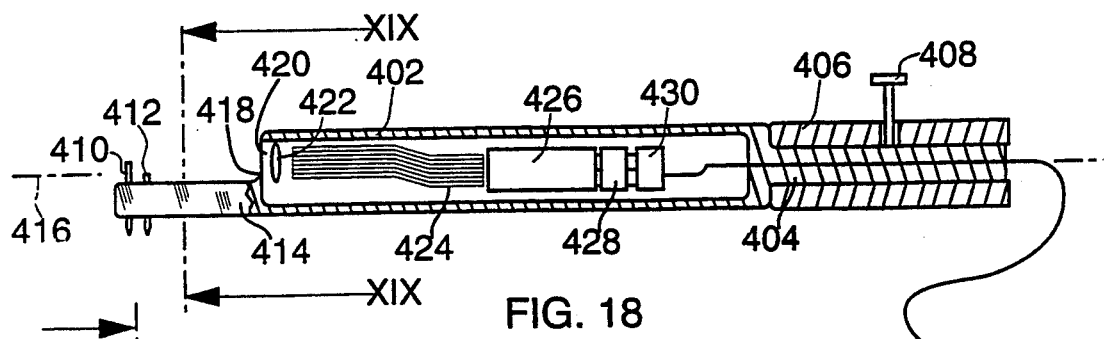
FIG. 18 is a side elevational view, partially in cross-section, of a hand held instrument usable in conjunction with a pantograph assembly illustrated in FIGS. 11-15, for gathering parallel contour data.

As illustrated in FIG. 18, a device for feeding to computer 24 (FIG. 1) contour data as to the surface of an object such as a tooth comprises a hand-held dental instrument or frame 402 provided at a proximal end with an extension 404 removably insertable into a sleeve 406 which forms a part of a pantograph assembly such as that illustrated in FIGS. 11 through 15. Instrument frame 402 is locked in a predetermined position and orientation to pantograph sleeve 406 by a set screw 408.

At a distal end, instrument frame 402 carries two sets of pins 410 and 412 slidably mounted to a nose portion 414 of instrument frame 401 in respective linear arrays extending at an angle, preferably a right angle, with respect to a longitudinal axis 416 of instrument frame 402.

Proximally of nose portion 414, instrument frame 402 has a shoulder 418 in turn formed with an opening or window 420 facing pins 410 and 412. A lens 422 is disposed at window 420 for focusing incoming light on an input end of a bundle of optical fibers 424 extending to a video camera in the form of a charge coupled device ("CCD") 426 inside instrument frame 402. CCD 426 is provided with conventional scanning circuitry 428 and output signal preprocessing circuitry 430. An output lead or multiple 432 extends from preprocessing circuitry 430 to computer 24 (FIG. 1).

Figure 19:
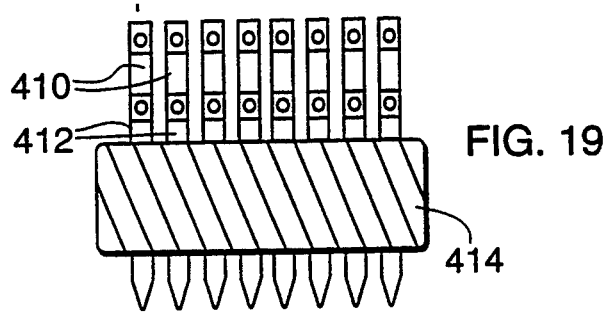
FIG. 19 is a cross-sectional view taken along line XIX—XIX in FIG. 18.
Figure 20:
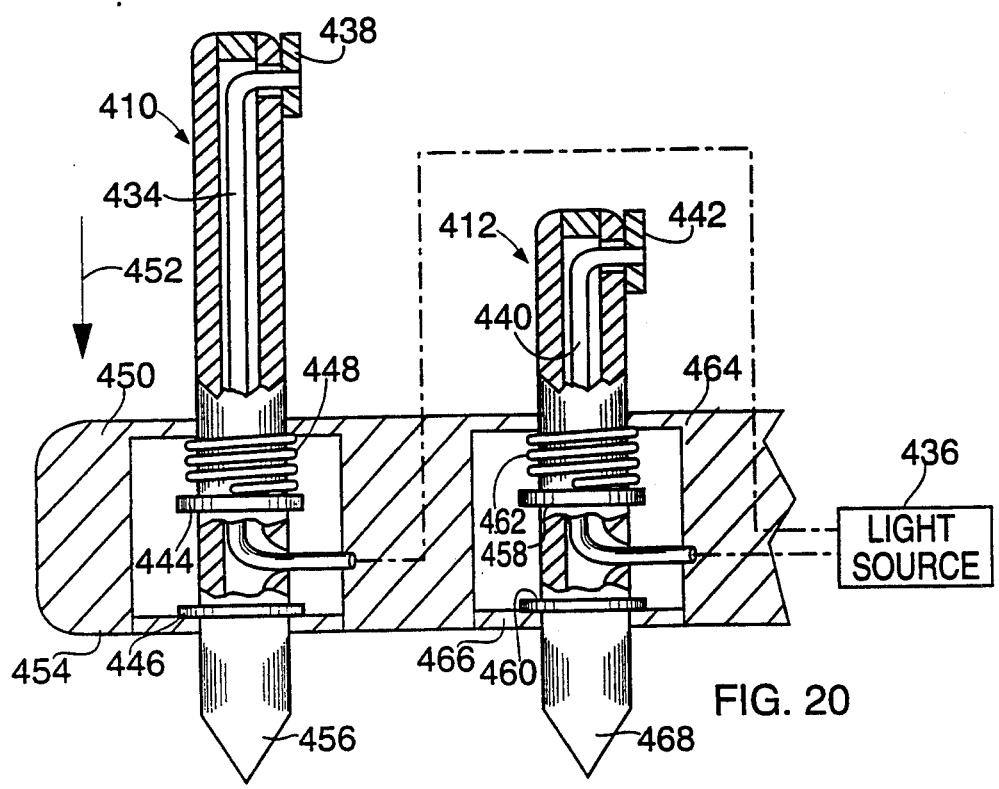
FIG. 20 is a partial cross-sectional view taken along line XX—XX in FIG. 19.

It is to be noted that other configurations of the operative components of the device of FIGS. 18-20 are possible. For example, CCD 426 and its associated circuitry 428 and 430 may be disposed at computer 24 or an intermediate location between the computer and instrument frame 402. In that configuration, optical fiber bundle 424 extends out from instrument frame 402 to the remote CCD. Alternatively, optical fiber bundle 424 may be omitted and CCD 426 positioned in juxtaposition to lens 422.

As depicted in FIGS. 19 and 20, each pin 410 is hollow and contains an end portion of a respective optical fiber 434 extending from a light source 436 inside instrument frame 402 to a mounting bracket 438 at an end of the respective pin 410. Each pin 412 is also hollow and contains an end portion of a respective optical fiber 440 extending from light source 436 to a mounting bracket 442 at an end of the respective pin 412. The distal ends of optical fibers 434 and 440, at mounting brackets 438 and 442, face lens 422, whereby the linear postions of pins 410 and 412 relative to nose portion 414 of instrument frame 402 may be instantaneously and continuously monitored by computer 24 through the video signals received from CCD 426.

As further depicted in FIG. 20, each pin 410 is provided with a pair of spaced perimetrically extending flanges 444 and 446. A helical spring 448 is compressed between a wall 450 of nose portion 414 and flange 444, thereby biasing the respective pin 410 in a direction indicated by an arrow 452. Flange 446 cooperates with another wall 454 of nose portion 414 to limit the distance that a pointed end 456 of the respective pin 410 projects from nose portion 414.

Each pin 412 is provided with a pair of spaced perimetrically extending flanges 458 and 460. A helical spring 462 is compressed between a wall 464 of nose portion 414 and flange 458, thereby biasing the respective pin 412 in a direction indicated by arrow 452. Flange 460 cooperates with another wall 466 of nose portion 414 to limit the distance that a pointed end 468 of the respective pin 412 projects from nose portion 414.

In using the contour data gathering device of FIGS. 18-20, a dental practitioner attaches the instrument frame 402 to pantograph-type component 50 (FIG. 1) via sleeve 406 and set screw 408, thereby fixing the instrument frame and pins 410 and 412 with respect to pantograph arm 56 which is monitored by optoelectrical transducers or video cameras 60 and 62. Pantograph component 50 enables computer 24 to track, from outside the mouth, the translatory motion of an arbitrarily selected reference point on instrument frame 402 inside the mouth of a patient. In addition, described hereinabove, pantograph assembly enables computer 24 to track the orientation of instrument frame 402 inside the patient's mouth. In this manner, computer 24 is continuously informed not only as to the position of the arbitrary reference point, but also the orientation of a coordinate system or reference frame, exemplarily with the reference point as origin.

It is to be noted that other methods for providing computer 24 with data as to the position and orientation of dental instrument 402 are possible. Instead of pantograph assembly, for instance, the encoders and articulated support arm assembly 310 of FIG. 14 may be utilized.

In addition to the data representing the location of an arbitrary reference point on instrument frame 402 inside a patient's mouth and the three-dimensional orientation of the instrument frame, computer 402 is supplied with a data stream from CCD 426 regarding the instantaneous positions of sliding pins 410 and 412. The dental practitioner presses pointed ends 456 and 468 of pins 410 and 412 against a dental surface and simultaneously draws instrument frame 402 along that surface. During this motion, pins 410 and 412 slide back and forth perpendicularly with respect to nose portion 414 in response to variations (pits and cavities, projections) in the surface of the tooth being scanned. These reciprocating motions tracing a plurality of parallel contours along the tooth surface are sensed by CCD 426 and quantized by computer 24 to form parallel contour data utilizable by conventional CAD/CAM programs previously loaded into computer 24.

The positional tracking of pins 410 and 412 by CCD 426 and computer 24 is facilitated by light output of optical fibers 434 and 440. Computer 24 measures the motions of pins 410 and 412 relative to the arbitrary reference point. Moreover, computer 24 is able to instantaneously correlate the incoming contour data stream(s) with the tooth surface being scanned, owing to the incoming rotational data as to the orientation of instrument frame 402 inside the patient's mouth.

Pins 410 and 412 are shown in FIG. 19 as being aligned with one another along the longitudinal axis 416 of instrument frame 402. However, contour data is collectible at an enhanced rate if the pins 410 of one row are staggered with respect to the pins 412 of the other row. Such a two-dimensional array of pins 410 and 412 enables a greater pin density, thereby increasing the amount of incoming contour data.

Instrument frame 402 may be provided with a button (not shown) which, when pressed by the dentist, provides computer 24 with a signal that contour data input is commencing.

Figure 21:
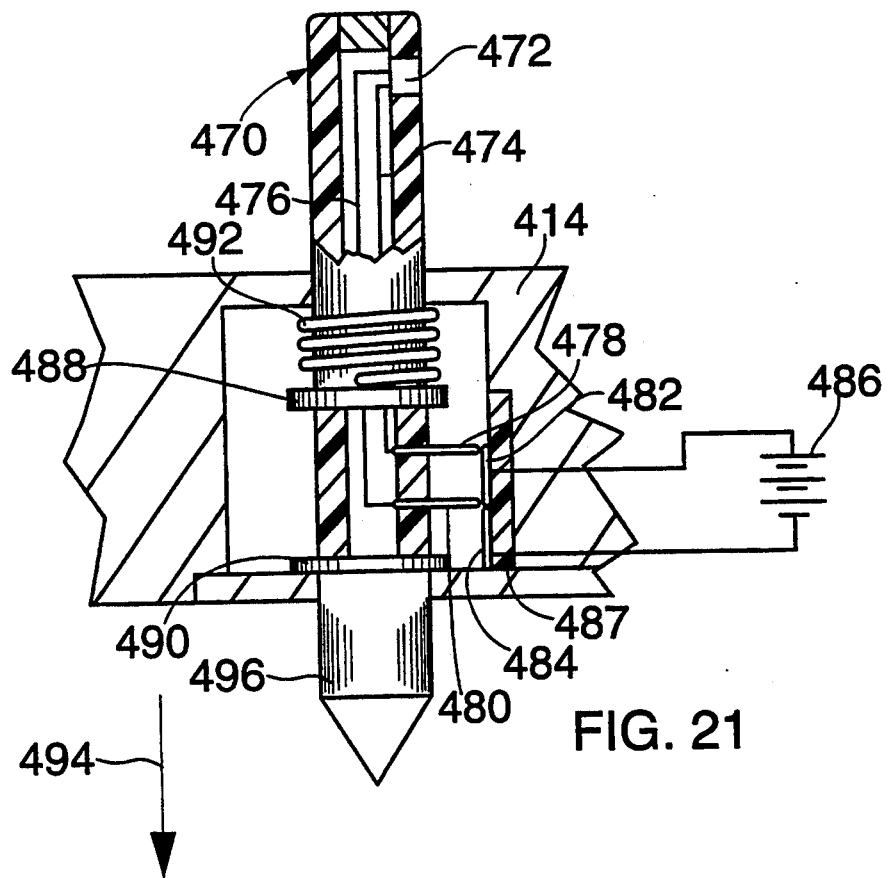
FIG. 21 is a partial cross-sectional view similar to that shown in FIG. 20, showing a modified parallel contour data gathering device.

FIG. 21 depicts another pin or stylus 470 slidably mounted to nose portion 414 of instrument frame 402 in substitution for pins 410 and/or 412. In pin 470, a light-emitting diode 472 forms the light source for facilitating detection by CCD 426 (FIG. 18) and monitoring by computer 24. Diode 472 is connected by a pair of leads 474 and 476 to two brush-type terminals 478 and 480 which are in sliding contact with respective plates 482 and 484. Plates 482 and 484 are connected to opposite terminals of a direct-current voltage source 486 and are insulated from nose portion 414 by a buffer element 487.

As further depicted in FIG. 21, each pin 470 is provided with a pair of spaced perimetrically extending flanges 488 and 490. A helical spring 492 is compressed between wall 450 or 464 (see FIG. 20) of nose portion 414 and flange 488, thereby biasing the respective pin 470 in a direction indicated by an arrow 494. Flange 490 cooperates with wall 454 or 466 of nose portion 414 to limit the distance that a pointed end 496 of the respective pin 470 projects from nose portion 414.

Figure 22:
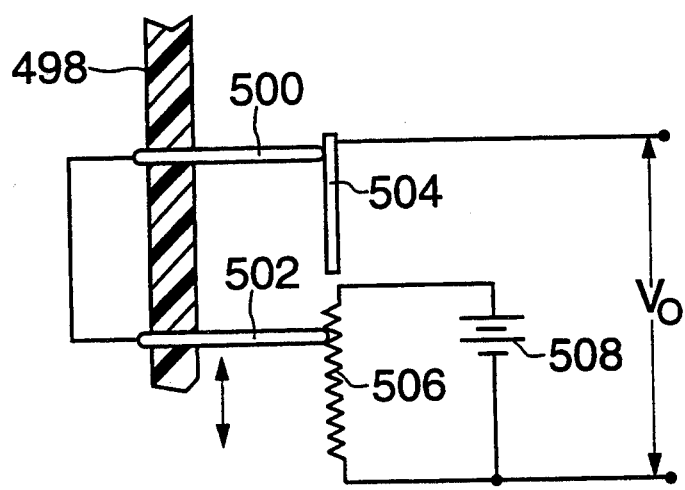
FIG. 22 is a diagram showing a circuit of another parallel contour data gathering device.

FIG. 22 illustrates a portion of a pin or stylus 498 slidably mounted to a nose portion (e.g. 414 in FIG. 18) of a dental instrument for providing computer 24 (FIG. 1) with digitized data representing a surface contour on a tooth. As described hereinabove with reference to FIGS. 18–20, pin or stylus 498 is one of a plurality of identical stylii all slidably mounted to the nose portion of the instrument frame in a linear or two-dimensional array for providing contour data along a plurality of parallel planes. As further described above with reference to FIGS. 18–20, the dental instrument carrying pins 498 is removably attachable to pantograph-type component 50 (FIG. 1), whereby computer 24 is also provided with digitzed data representing the location and orientation of a distal end of the dental instrument inside a patient's mouth during use of the dental instrument.

A pair of brush type contacts 500 and 502 are embedded in stylus 498 and operatively engage in a sliding contact a plate 504 and a resistive element 506, respectively. A direct-current voltage source 508 is connected across resistive element 506, while an output voltage $v_O$ is taken across a portion of resistive element 506 depending on the distance that stylus 498 is shifted with respect to the instrument. Output voltage $v_O$ thus represents the displacement of stylus 498 and is fed to an analog-to-digital converter (not shown) prior to being fed to computer 24.

As shown in FIG. 23, a parallel contour data gathering device includes an instrument frame or body 510. A nose portion 512 is pivotably attached to a distal end of frame 510 for rotation about an axis 514. Nose portion 512 carries two linear arrays of pins or stylii 516 and 518 slidably mounted to the nose portion as described hereinabove with reference to FIGS. 18–20. Pins 516 and 518 are partially longitudinally traversed by respective optical fibers 520 and 522 extending from a diode 524 in nose portion 512. Diode 524 in turn is energized by a source of electrical power via a pair of leads 526. Leads 526 include a pair of sliding or brush type contacts 528 for enabling the conduction of electrical energy to diode 524 over the rotating link between frame 510 and nose portion 512.

A reciprocating type motion of pins 516 and 518 which occurs as a dentist moves nose portion 512 along a tooth surface is monitored by computer 24 via digitized video signals arriving from a charge-coupled device ("CCD") and its associated circuitry 530. CCD 530 receives optical energy via a bundle of optical fibers 532 extending from a lens 534 in nose portion 512.

The pivoting attachment of nose portion 512 to frame 510 facilitates the collection of parallel contour data by enabling a dentist to orient nose portion at an angle (e.g. a right angle) with respect to a longitudinal axis 536 of instrument frame 510. The angular orientation of nose portion 512 particularly facilitates the collection of parallel contour data along a plurality of parallel planes oriented at the aforementioned angle with respect to axis 536. Computer 24 is able to take the orientation of nose portion 512 into account by monitoring, via pantograph assembly 50, the direction of motion of the distal end of instrument frame 510 during a data gathering motion thereof.

In addition to being preprogramed with digitized representations of dental preparation preforms in different sizes and shapes, corresponding to actual preforms in a kit, computer 24 may be preprogramed with digitized images of intermediate stages in the preparation of teeth to receive the preforms. Thus, each preform in the kit of preforms has in the data memory of the computer 24 a plurality of digitized images, one image representing the preform itself and other images representing intermediate stages or steps in the preparation of the tooth or teeth with which the preform may be used.

Upon the input into computer 24 of digitized data defining the surface of a tooth and upon the selection of a tooth preparation or preform either automatically by computer 24 or in response to instructions received via keyboard 40, computer 24 displays on monitor 34 an image of the tooth, an image of the selected preparation, and an image of an intermediate stage or step in modifying the tooth to attain the selected preparation. These images may me shown sequentially or simultaneously in juxtaposition to one another on the monitor. In addition, the images may be modified, for example, in response to instructions from keyboard 40, to show different perspective views and/or cross-sectional views of the tooth, the selected preparation, and the intermediate stage. Of course, more than one intermediate stage may be shown, if such a multiple display is helpful in graphically explicating the modification of the tooth to achieve the desired structure. It is to be noted that successive intermediate stages may be displayed simultaneously in juxtaposition to each other. Alternatively, the successive stages may be displayed sequentially.

Upon the display on monitor 34 of one or more intermediate stages in the modification of a tooth to achieve the displayed preparation, the dental practitioner operates drill 38 (FIG. 1) to modify the subject tooth initially to attain an intermediate stage and subsequently to reach the final desired preparation.

Of course, as discussed hereinabove with respect to the displayed graphic representation of the tooth, the displayed intermediate stage may be modified by computer 24 in response to instructions from the dental practitioner. Such an on-screen modification would preferably be implemented prior to undertaking a tooth preparation operation.

It is to be noted that the above-described technique for using computer assistance in modifying the shape of a tooth is especially useful to teach students preferred steps in preparing a tooth. Computer 24 is preprogramed to store in encoded form a plurality of possible final modifications or preparations of a tooth and for each such final preparation at least one respective intermediate stage in modifying the object at its surface to attain the respective modification.

As described hereinabove, the modification of the tooth in accordance with the preprogramed intermediate stage data may be implemented automatically by computer 24 operating under numerical control. Computer 24 thus uses the drill movement control assembly 230 described above with reference to FIG. 15.

It is to be understood that the modification of the tooth may be implemented by a machining or drilling process or more modern techniques such as laser etching.

Pantograph assembly 50 or, alternatively or additionally, encoders and articulated support arm assembly 310 provide a system and procedure for automatically and precisely monitoring the motions of a dental instrument as it is being manipulated, either inside or outside the mouth of a patient. As described hereinafter, the motions and/or positions and orientations of the dental instrument may be recorded for subsequent playback or display on monitor 34. This playback is advantageous, for example, for pedagogical purposes. A skilled dentist or dentistry teacher uses a dental instrument to execute a preferred or ideal technique, and successive positions and orientations of the instrument are input into a computer via pantograph assembly 50 and its attendant cameras or, alternatively or additionally, encoders and articulated support arm assembly 310. Thus, these motion digitization devices are used to digitize the entire motion of a dental instrument or other tool as it approaches and begins work on an object (e.g., tooth) to be modified (e.g., machined or drilled). To receive and store the motion-encoding digital signals, computer 24 need only be programmed to recognize when such motion input is occuring. Recognition may be triggered, of course, by appropiate input, for example, via keyboard 40 (FIG. 1).

The initial recordation of a preferred manner of holding the dental instrument (which may be an operating instrument such as a drill or a non-operative instrument such as a periodontic probe) may be implemented using a model or a representative tooth.

Upon the storage of motion data, computer 24 uses the data to illustrate the motion on monitor 34. Such a depiction of instrument motion may take the form of a series of discrete images of different successive positions and orientations of the dental instrument. The successive images may be shown in rapid succession, as in a video presentation, or in slow motion. Alternatively, the successive positions and orientations may be displayed simultaneously in juxtaposition on monitor 34. As yet another alternative, particularly in the event that one position and orientation of the dental instrument is sufficient to demonstrate the preferred instrument use, computer 24 may be operated to show only that one position and orientation of the dental instrument. In addition, to further illustrate the manipulation of the instrument, a graphic representation of a hand holding the instrument is shown on monitor 34. In the event of several successive images, the hand's orientation may change together with the orientation of the instrument.

Upon (a) the feeding to computer 24 of digitized information as to a surface of a tooth, (b) showing on a display a graphic representation the tooth or a portion thereof and possibly a graphic representation of a selected tooth preparation, and (c) the display on monitor 34 of one or more images of a dental instrument in a preferred orientation for accomplishing a desired modification of a tooth to achieve, for example, a selected preparation, the dental practitioner or student manipulates drill 38 (FIG. 1) or a mock drill (e.g., with a telescoping or self-sinkable drill bit) in an attempt to replicate the displayed position and orientation or series of displayed positions and orientations. During this exercise, computer 24 advantageously monitors the motion via pantograph assembly 50 or, alternatively, encoders and articulated support arm assembly 310. Computer 24 compares the actual motion with the ideal motion, as stored in memory, and displays the results of the comparison on monitor 34. Such results may take the form, for example, of two differently colored images or sets of images. In addition, arrows or other pointers may be used to indicate parts of the actual motion which could be changed in a subsequent exercise to closer approximate the ideal motion. Of course, an auditory alert signal may be generated by computer 24 to indicate deviation from the ideal motion. The alert signal is advantageously sounded during the manipulation of the instrument. As the instrument deviates further and further from the ideal path, the auditory signal may become louder, or change in pitch.

The providing of feedback to a practitioner or student thus includes the step of displaying a graphic representation of at least one actual position and orientation of the instrument attained during the manipulation of the instrument. The graphic representation can be displayed in juxtaposition to the image of the ideal position and orientation of the instrument.

In providing feedback, computer 24 advantageously quantizes differences between the ideal position(s) and orientation(s) and actual positions and orientations taken by the instrument during manipulation of the instrument by the dentist or studnet. The quantized differences are indicated to that person via monitor 34.

Figure 24:
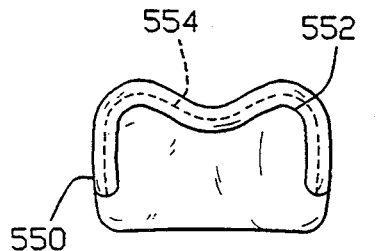
FIG. 24 is a schematic side elevational view of a tooth as it would appear on a computer monitor in accordance with the present invetntion, showing a desired preparation of the tooth and an intermediate stage in the actual preparation.

FIG. 24 represents a graphic representation of a tooth 550 shown on computer monitor 34 (FIG. 1). The external surfaces of tooth 550 are digitized and stored in internal memory of computer 24, as described hereinabove with reference to FIGS. 1–23. In addition, as also described above, computer 24 is operated to select a digitized or electronic preform 552 from an inventory of preparations stored in computer 24. The inventory of electronic preforms advantageously corresponds to a kit of actual preforms which may be inserted into actual preparations upon the formation of the preparations in patient's mouths by a dental practitioner.

Upon selection of preparation 552, either automatically by computer 24 or by the practitioner utiliizing keyboard 40 (FIG. 1), preparation 552 is displayed in overlay on tooth 550 on monitor 34. Preferably, preparation 552 is displayed in a different color from tooth 550.

Although FIG. 24 shows only a single view of tooth 550. It is to be understood that several views may be displayed on monitor 34 simultaneously. For example, tooth 550 may be shown in buccal or lingual elevation, from the mesial direction or in plan view. In addition, one or more cross-sectional views of tooth 550 may be provided. These views may be presented as a matter of course on monitor 34 or, alternatively, the practitioner may instruct computer 24 as to which views are to be displayed. Preferably, the tooth and preparation 552 have the same respective colors in all the various views.

Upon the display of tooth 550 and preparation 552 on monitor 34, the practitioner uses drill 38 (FIG. 1) to modify the patient's tooth 550 pursuant to the desired preparation 552 as displayed on monitor 34. During the modification of the actual tooth, the graphic representation on monitor 34 is altered to conform to the new tooth surfaces, as shown at 554. The new tooth surface 554 is preferably displayed in a color different from the colors of the original surfaces of tooth 550 and the surfaces of preparation 552.

To provide the practitioner with an additional indication of how close the prepared tooth surfaces 554 are to the desired or target preparation 552, the color selected by computer 24 for the new tooth surface 554 corresponds to the distance between the actual tooth surface 554 and the desired preparation surface 552. As the distance between the actual tooth surface 554 and the desired preparation surface 552 changes during the dental operation, the color of new surface 554 on monitor 34 changes. To this end, computer 24 is provided with a preprogramed sequence or palette of selectable colors which may, for example, represent sequential half-drill diameter distances. Thus, it is easy to determine by a glance at monitor 34 the status of a preparation in progess. Of course, computer 24 is programed to continuously calculate distances between the actual tooth surface 554 and the desired preparation surface 552 and to select the color of new surface 554 in accordance with the colors of the palette.

Figure 25:
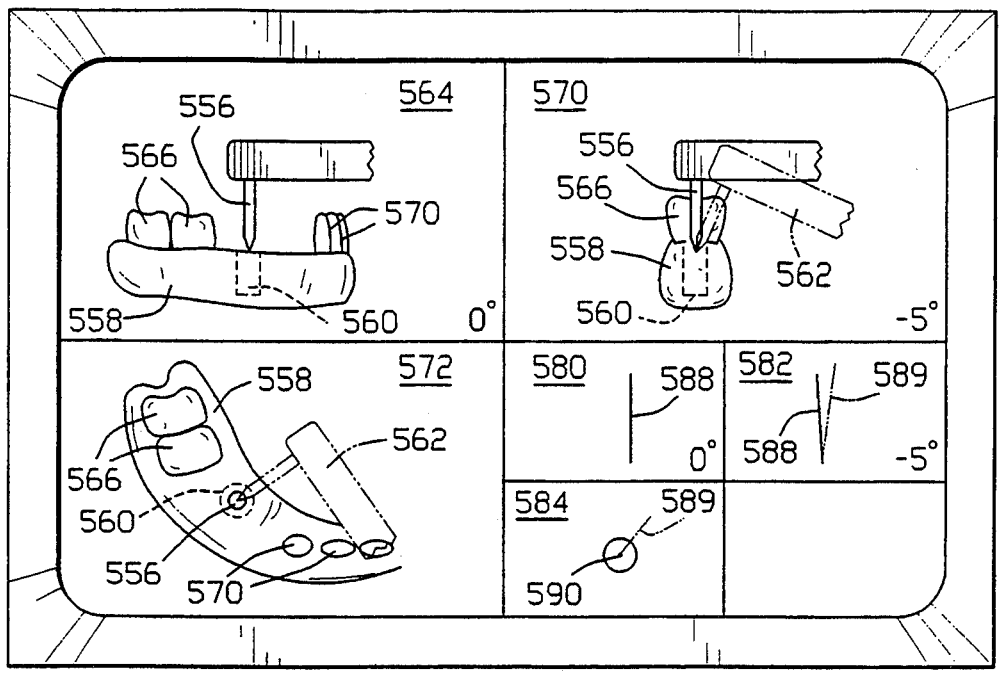
FIG. 25 is a display on a computer monitor, showing optimal and actual orientations of a dental instrument relative to a patient's dentitious surfaces.

FIG. 25 shows a display on monitor 34 of three views of an optimal position and orientation 556 of a drill (not separately enumerated) for cutting into a patient's mandible 558 (or any bone structure) a bore 560 for receiving an anchor or blade (not shown) of an implant. FIG. 25 also illustrates in dot-dash phantom outline an actual position and orientation 562 of the drill during an actual operation, or of a virtual instrument during a practice or trial run.

More specifically, a first screen portion 564 illustrates a buccal or lingual elevational view of a pair of molars 566 and several front teeth 568, as well as a part of jaw bone 558. In a second screen portion 570 is depicted a view of molars 556 from the mesial direction. In a third screen portion 572 is a top plan view of molars 566, front teeth 568 and bone 558. As discussed hereinabove with reference to FIG. 24, other views may include cross-sectional views which are dervied by computer 24 via interpolation techniques.

The external surfaces of teeth 566 and 568 are measured or digitized as described above with reference to FIGS. 1–23. In addition, stylus or probe member 52 (FIG. 1) is used to digitize the surface of jaw bone 558. To that end, stylus member 52 is provided with a sharp stylus 574 (FIG. 1) having a length sufficient long to penetrate gum tissue and contact the bone surface. Upon achieving a contact, the practitioner signals computer 24, e.g., via keyboard 40. The dental practitioner repeats the procedure of piercing the gum tissue in a region about a desired implantation site and taking point data until enough data has been collected for computer 24 to map, via interpolation techniques, the entire surface of bone 558 about the implantation site.

The exact placement of bore 560 may be determined to a greater or lesser extent automatically by computer 24. Computer 24 makes this determination in accordance with (a) surface data as to molars 566 and front teeth 568, (b) surface data as to opposing teeth (bite information, obtained as described hereinafter particularly with reference to FIG. 31), (c) the dimensions and shape of jaw bone 558, and (d) the location of internal bone structures, such as blood vessels such those which occupy inferior alveolar canals, or sinus structures, which are to be scrupulously avoided during the drilling operation. It is to be noted that computer 24, because of the digitized locations of and shape data on the canals and sinuses or other anatomical structures, is in an excellent position to determine the optimal angle and depth of anchor-receiving bore 560.

Data as to internal structures (e.g., blood vessel canals) of jaw bone 558 may be obtained via X-ray data generating device or assembly 28 (FIG. 1). Such internal structures can be displayed on monitor 34. The coordination of the X-ray data as to internal structures and the data collected via optical data generating device or assembly 22 and pantograph data generating device or assembly 26 is implemented as described hereinafter with reference to FIG. 29.

As stated above, computer 24 calculates an optimal position and orientation 556 of a drill for forming bore 560 and displays that optimal position and orientation preferably, although not necessarily, in three orthogonal views such as the buccal or lingual elevational view of screen portion 564, the mesial direction view of screen portion 570, and the top plan view of screen portion 572. To enable a dentist or oral surgeon to practice holding the drilling instrument in the correct position and orientation 556, the drill is attached to the pantograph assembly (e.g., like cutting instrument 38 in FIG. 1). Alternatively, a practice or virtual instrument as those discussed hereinafter with reference to FIGS. 26 and 27 may be attached to the pantograph assembly.

The dentist holds either the actual drilling instrument or a practice instrument in the patient's mouth and manipulates it while watching monitor 34. On monitor 34, the position and orientation 562 of the manipulated instrument is represented in real time in a manner detectably different from the representation of the optimal position and orientation 556 of the drill. For example, the actual position and orientation 562 of the actual or practice instrument may be shown in a different color or in phantom outline, as in FIG. 25.

As shown in FIG. 25, a dentist or oral surgeon is provided with immediate feedback, from at least two different directions, of the position and orientation of an actual or virtual drill relative to the patient's tooth and bone surfaces. This feedback also includes an indication of the actual position and orientation 562 relative to a predetermined optimal position and orientation 556. The indication may include not only an illustration of the relative positions and angles but also numerical angular designations (e.g., 0°, −5°) of the differences between the actual position and orientation 562 relative the predetermined optimal position and orientation 556.

As further illustrated in FIG. 25, the display on monitor 34 may also include one or more screen areas 580, 582 and 584 wherein the representations of the actual position and orientation 562 and the predetermined optimal position and orientation 556 are simplified to lines 588, 589 and points 590.

The feedback as to divergences between actual position and orientation 562 and predetermined optimal position and orientation 556 may alternatively or additionally take an aural form, instructions or information being communicated to the dentist or surgeon via electro-acoustic transducer 44 (FIG. 1). If the instructions or information is in the form of words, those words may be generated with the aid of well known, conventional speech synthesis software and hardware (not illustrated).

Figure 26:
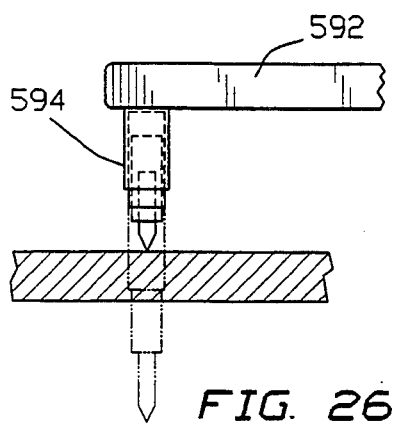
FIG. 26 is a side elevational view, on an exagerrated scale of a dental instrument with a telescoping virtual operating tip.

A virtual instrument for use in practice or trial runs is depicted in FIG. 26. The instrument includes a handle 592 attachable to pantograph component 64 (FIG. 1) and a virtual operating tip 594 comprising a telescoping member. Telescoping operating tip 594 enables the dentist or surgeon to practice a drilling operation on the patient without actually penetrating the patient's tooth or tissues (e.g., gingiva, edentulous gum tissue or bone tissue). As discussed above, the dentist or surgeon watches monitor 34 during the practice or trial run, thereby obtaining immediate feedback as to the proper manipulation of the instrument.

Upon satisfactory practice, the dentist or surgeon replaces the practice instrument (FIG. 26) with an implant burr or drill and proceeds with the actual operation. Of course, computer 24 continues to provide both visual and aural feedback to the operator during the actual surgery.

The supplementary techniques described above for computer monitoring of a dental operation are available in an implant operation. Computer 24 may terminate power to the drilling instrument if the angle of penetration deviates more than a preset amount from the predetermined optimal orientation. Alternatively, the drilling operation may be conducted automatically by computer 24 in accordance with the principles of numerical control and with the equipment described above with reference to FIG. 15.

As also described earlier, the dentist or surgeon interacts with computer 24 to determine the optimal position and orientation 556. A selection made by computer 24 may be modified by the practitioner. Moreover, the selection by the computer may be made in accordance with a digitzed inventory of anchors and angle.

It is to be noted that this technique of practice or trial run operations may be performed in areas of surgery other than dental surgery. Generally, the necessary steps include (a) scanning body structures internal to the patient, (b) digitizing the internal structures in response to the scanning, (c) displaying an image of the internal structures in response to the digitized signals, (d) providing a practice surgical instrument with a virtual operating tip, (e) moving the surgical instrument outside of the patient in a simulation of actual surgery on a portion of the internal structure, (f) automatically monitoring the instrument during the step of moving, and (g) displaying a representation of at least the operating tip of the instrument in overlap with the image of the internal structure during the step of moving.

Figure 27:
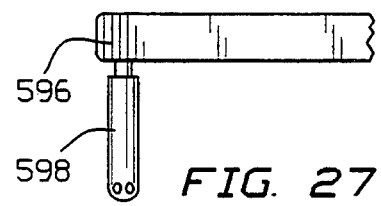
FIG. 27 is a side elevational view of another dental instrument for use in a practice or virtual operation.

As shown in FIG. 27, practicing an implant procedure may be undertaken with a dental instrument provided with a holder 596 to which an implant anchor 598 is attached. This provides the practitioner with further visual and tactile feedback as to the position and orientation that the anchor will have upon implantation into jaw bone 558 of the patient. The instrumentation shown in FIG. 27 may be modified for placing an implant anchor into a telescoping frame so that actual pressing of the implant into tissue provides a graphic display of the virtual position of the implant as it would be inserted.

Figure 28:
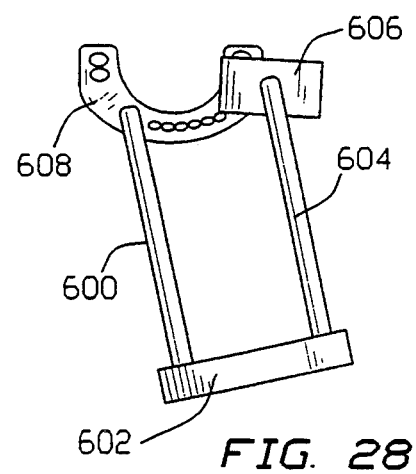
FIG. 28 is a schematic top plan view of an instrument assembly being used in performing a dental surgical method.

As illustrated in FIG. 28, a practice or trial run of an implant drilling operation may be performed with a practice or virtual instrument 600 mounted to a pantograph assembly 602 which also holds a drill 604. Drill 604 is enslaved to virtual instrument 600, as described hereinabove with respect to FIGS. 1 and 14, so that motions of virtual instrument 600 are duplicated by drill 604. During motions of virtual instrument 600 towards jaw bone 558, as if an actual operation were being performed, drill 604 cuts a bore into a block of acrylic material 606 which has been fastened to the patient's jaw by conventional bonding techniques.

Upon the satisfactory completion of a practice operation, block 606 is provided with a hole (not shown) matching the bore 560 to be formed in the patient's jaw bone 608. The hole in block 606 can then be used as a template to guide, limit or control the motions of an implant drill during an actual operation on the patient's jaw bone 558. Prior to the actual operation, of course, virtual instrument 600 is replaced by an actual implant drill while a drone or probe is substituted for drill 604 in pantograph assembly 602.

As described hereinabove, the system of FIG. 1 includes (a) optical data generating device or assembly 22 for providing a computer 24 with electrically encoded data, specifically, digitized video signals representing a three-dimensional surface of an object such as a tooth, (b) pantograph data generating device or assembly 26 for providing computer 24 with digitized signals containing information pertaining to a curvilinear contour on the surface of the three-dimensional surface of the tooth, and (c) X-ray data generating device or assembly 28 for providing computer 24 with digitized input signals relating to internal structures of the tooth and surrounding anatomy being scanned.

Figure 29:
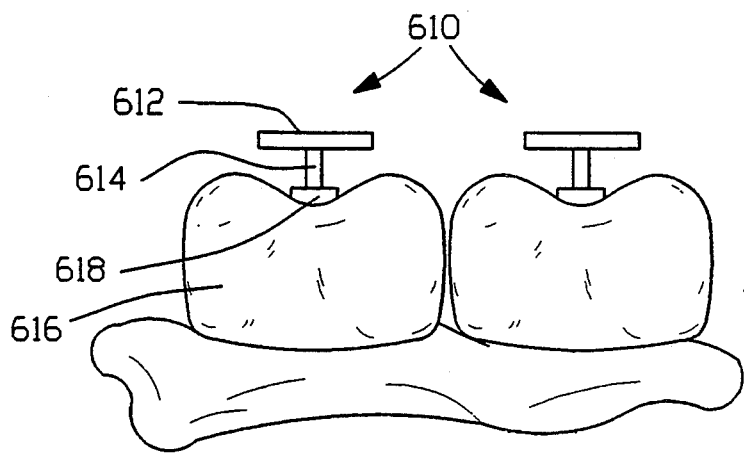
FIG. 29 is a side elevational view of a pair of molars bearing fiducial coordinate frame reference elements.

In order to coordinate the data from optical data generating device or assembly 22 and/or pantograph data generating device or assembly 26, on the one hand, with the data from X-ray data generating device or assembly 28, on the other hand, it is desirable to provide computer 24 with reference data to establish a common coordinate system for both the external surface data from devices or assemblies 22 and/or 26 and the internal structural data from X-ray device 28. As illustrated in FIG. 29, this common coordinate system may be established via the utilization of fiducial reference elements 610 each comprising an X-ray opaque or X-ray detectable portion 612 in the form of a cross-bar of a T shape. The X-ray opaque cross-bar 612 is connected to an X-ray transparent stem 614 in turn cemented to the occlusal surface of a respective tooth 616 at 618. The locations and orientations of reference elements 610 with respect to the external surface data are determined via the use of pantograph data generating device or assembly 26. That device merely traces the shape of cross-bar 612 or a predetermined feature on the surface of the respective reference element 610. The teeth to which the particular coordinate-system reference elements 610 are attached may be entered in computer 24 via keyboard 40. In addition, the identities of the teeth are communicated to computer 24 via X-ray data generating device or assembly 28. Reference elements 610 are provided with distinguishable identifying features detectable via X-ray data generating device or assembly 28. Such identifying features may take the form of a bar code or other markings.

Although FIG. 29 shows T-shaped reference elements, it is to be understood that numerous other shapes may be used.

Figure 30:
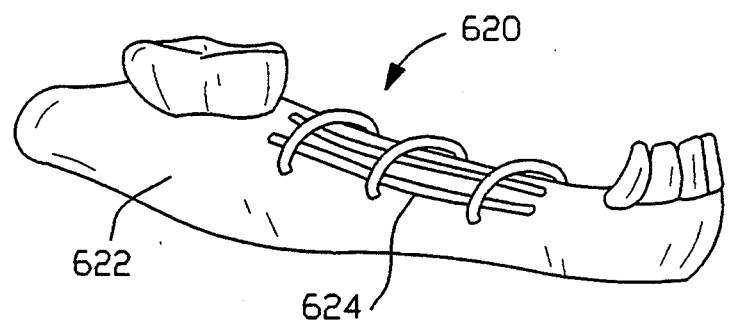
FIG. 30 is a perspective view of another fiducial coordinate frame reference element.

FIG. 30 depicts a coordinate-system reference element 620 in the shape of a saddle mounted on a gum surface 622. Reference element 620 may include one or more X-ray opaque segments or strips 624. The strips may include a bar code or other identification corresponding to the location of gum surface 622.

Data fed to computer 24 via X-ray data generating device or assembly 28 may comprise two or more views of the same tooth from different angles. In that event, computer 24 can use a stereophotogrammetric triangulation program to determine the three-dimensional shapes and dimensions of structures internal to the subject tooth. Alternatively, the thicknesses of internal structures such as roots and nerves may be calculated by computer 24 from the X-ray detectable dimensions and shapes (e.g., widths and lengths) and from statistics correlating the width and length dimensions with thickness dimensions for the diferent kinds of internal tooth structures. It is to be understood that roots are considered internal structures in this regard because of their dispositions inside the jaw bones.

As yet another alternative, the thicknesses of internal structures may be determined by computer 24 by from X-ray detectable densities. The gray level of a particular feature is therefore indicative of the thickness of that feature.

Computer 24 analyzes external surface data from optical data generating device or assembly 22 and/or pantograph data generating device or assembly 26 and internal structure data from X-ray data generating device or assembly 28 to determine three-dimensional dentitious structures. Computer 24 may be programmed additionally to recognize shapes, X-ray densities, textures, and relative locations of different structures in order to identify the different internal tooth structures. Upon identifying the different structures, computer 24 reproduces the structures in graphic form on monitor 34, as illustrated in FIG. 31.

Figure 31:
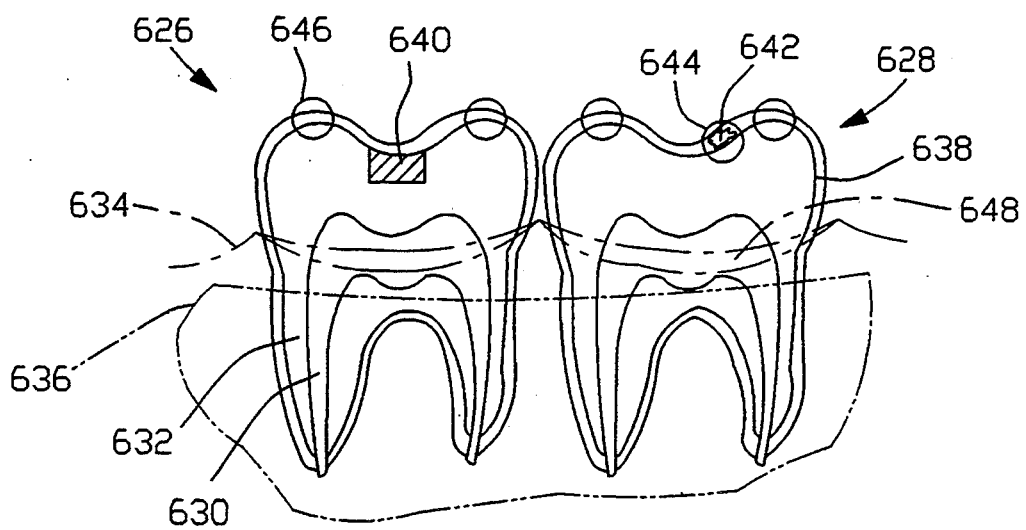
FIG. 31 is a graphic representation, as would appear on a computer monitor, of internal and external structures of a pair of molars.

More particularly, FIG. 31 illustrates an image which computer 24 provides on monitor 34. The image in FIG. 31 is a lingual or buccal elevational view of a pair of molars 626 and 628. Preferably, the different structures of molars 626 and 628, such as the root 630, the pulp 632, the gum 634, the bone 636, and the enamel 638 are displayed in different colors. Alternatively, cross-hatching, different line types and/or different textures may be used to distinguish the different structures.

In addition to natural substructures, computer 24 is programed to detect and display on monitor 34 abnormal conditions such as a filling 640 in molar 626 and decay 642 on molar 628. These abnormal conditions may be indicated in respective colors different from the colors used to indicate the normal tooth substructures. In addition, a circle 644 may be used to highlight a tooth condition, such as decay 642, particularly if the condition is small and possibly undetectable on monitor 34.

As described hereinabove with reference to FIG. 24, computer 24 may display, at the option of the user, many different views of the subject teeth 626 and 628. The views may be elevations or plan views or cross-sections. One or more views may be shown one the same screen at once. The view of the subject tooth or teeth 626, 628 may be a perspective view which is rotating in space, as shown on monitor 34.

Different numbers of teeth may be shown on monitor 34. depending on the preference of the user. One tooth may be selected or even all of the teeth of one or both jaws. In the latter case, the information displayed advantageously includes bite information such as the locations of contact between the occlusal surfaces. Such areas of contact may be highlighted by circles 646 (FIG. 31) or by other means.

Computer 24 is additionally programmed to calculate stresses on jaw bones and root structures, depending on the locations of the bite points on the different teeth, the types and sizes of the teeth and statistics as to bite forces. The statistical information may be replaced by measurements of a particular patient's bite.

Another dentitious dimension which may be determined and displayed on monitor 34 is the depth of gingival pockets 648 (FIG. 31). Pantograph data generating device or assembly 26 is particularly adapted to measure pocket depths and collect sub-gingival data. The pocket depths may be calculated by computer 24 in response to the digitized contour data from pantograph data generating device or assembly 26 and displayed in numerical or other coded form on monitor 34.

As shown in FIG. 1, computer 24 is connected at an input to a voice-recognition unit 650 which in turn receives input signals from an acousto-electric transducer 652, for example, a microphone. Transducer 652 and voice-recognition unit 650 are used by a practitioner to facilitate the input of data into computer 24. Generally, as the practitioner is providing computer with surface data from optical data generating device 22 or pantograph data generating device 26 or X-ray data from X-ray data generating device 28, the practitioner may be vocally identifying the teeth and/or the surfaces to which the surface data or X-ray data pertain. For example, the practitioner might say "tooth number 24, occlusal." In addition, as the dentist identifies a condition or abnormality such as a filling or decay, these characteristics may also be identified to the computer. For example, upon pointing to a particular location with stylus or perio-probe for coordinate output then in conjunction with this data generating device 26, the practitioner will say "decay, tooth number 18, buccal" to facilitate identification of the abnormality by the computer.

These conditions are then depicted on monitor 34 as described hereinabove with reference to FIG. 31. The convenience and facility of vocalization to diagnosis and charting may be readily understood.

Figure 32:
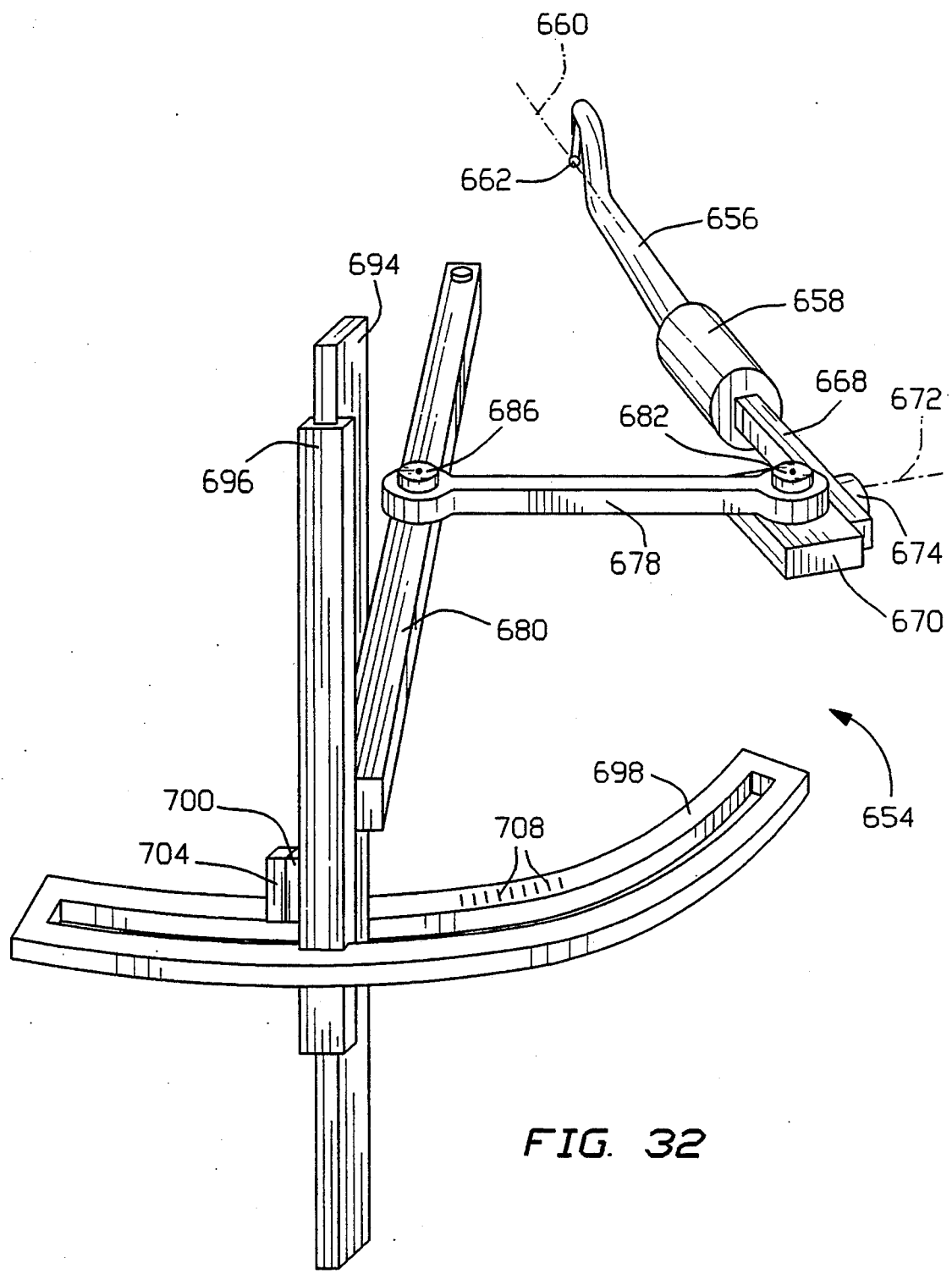
FIG. 32 is a schematic perspective view, on an enlarged scale, of another surface data generating device in accordance with the present invention.
Figure 33:
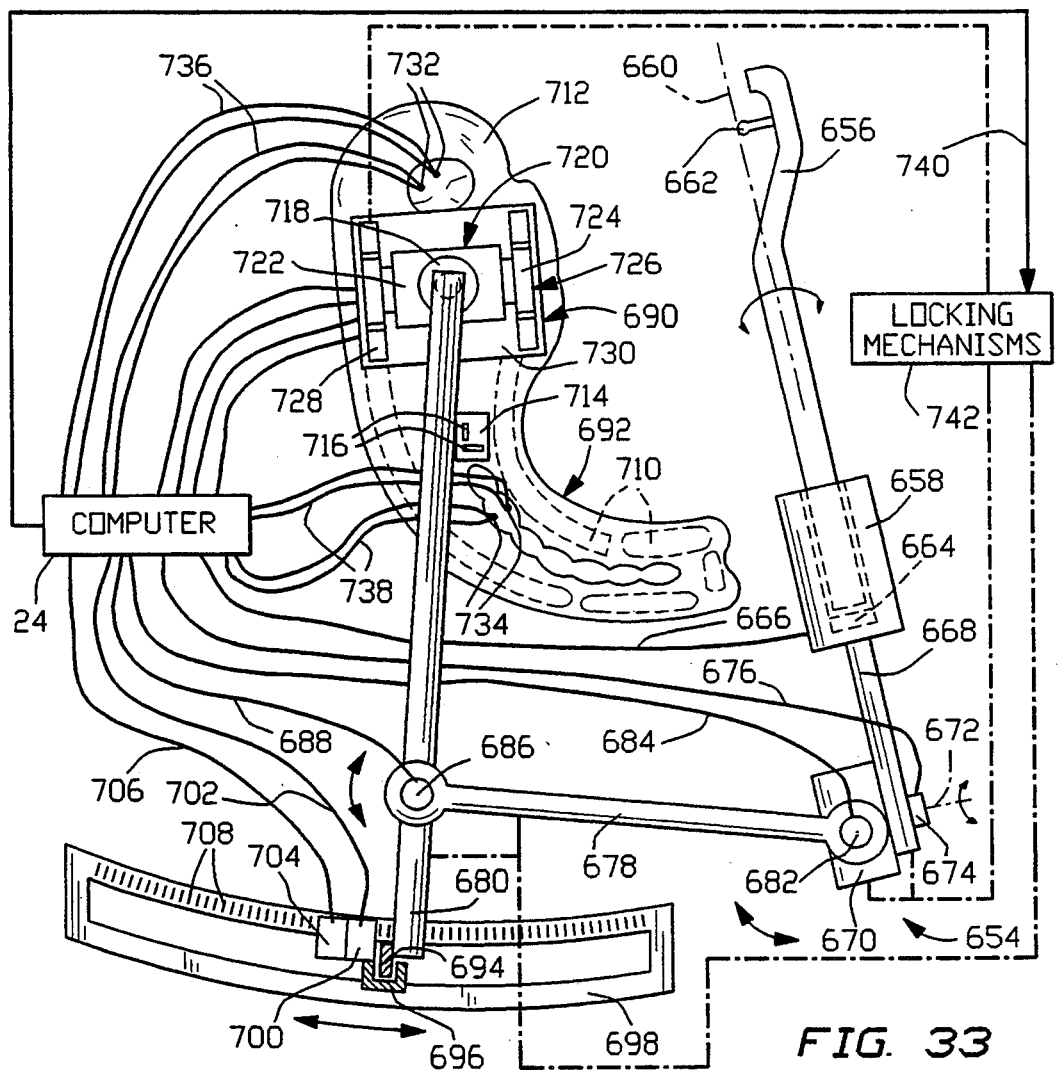
FIG. 33 is a schematic top plan view of the surface data generating device of FIG. 32, showing attachment of the device to a bite block, in accordance with the present invention.

FIGS. 32 and 33 illustrate a surface or contour data generating assembly utilizable in addition to or in place of the contour data generating devices of FIG. 11 and 14. The surface data generating assembly of FIGS. 32 and 33 is temporarily attachable to a patient's jaw, as described in detail hereinafter, and comprises an articulated arm assembly 654 wherein a probe instrument 656 is removably and rotatably mounted to a cradle 658. While seated in cradle 658, probe instrument 656 is manually rotatable about a longitudinal axis 660 passing through a contact tip 662 of the probe. The angular position of probe instrument 656 about axis 660 is monitored by a rotary encoder 664 and transmitted in electrically encoded form to computer 24 via a lead 666.

Cradle 658 is fixed to a first arm segment 668 in turn pivotably mounted at a rear end to a connector block 670. The rotary movement of arm segment 668 about an axis 672 relative to block 670 is monitored by a rotary encoder 674 and transmitted in electrically encoded form to computer 24 via a lead 676. Block 670 is rotably connected to a second arm segment 678 which is in turn pivotably mounted to a third arm segment 680. The rotational motion of block 670, and accordingly arm segment 668, with respect to arm segment 678 is detected by a rotary encoder 682 which is coupled to computer 24 via a lead 684. Similarly, relative rotation between arm segments 678 and 680 is sensed by another rotary encoder 686 connected to computer 24 via a rspective lead 688.

Arm segment 680 is temporarily fastened at one end to a person's jaw via a universal joint 690 (FIG. 33) and a bite block 692 which is custom fitted to the patient's jaw. At an opposite end, arm segment 680 carries an elongate arcuate rail 694 slidably seated inside an arcuate channel member 696 for motion in a circular arc along the channel member. Channel member 696 is in turn slidably mounted to an arcuate slotted track element 698 for motion therealong in a direction perpendicular to the motion of rail 694 relative to channel member 696. The motion of rail 694 along channel member 696 is monitored by an encoder 700 fixed to channel member 696 and connected to computer 24 via a lead 702. The motion of channel member 696 along track element 698 is measured by another encoder 704 also fixed to channel member 696 and connected to computer 24 via another lead 706. In the event that encoders 700 and 704 are optical sensors, rail 694 and track 698 may be provided with calibrations or markings 708 detectable by the sensors.

Upon attachment of articulated arm assembly 654 to a person's jaw via universal joint 690 and bite block 692, computer 24 is able to track the orientation and position of probe instrument 656, and consequently the position of tip 662, relative to the person's jaw. Accordingly, computer 24 is able to obtain electrically encoded data completely specifying the three dimensional surface structure of teeth and gums not covered by bite block 692. The electrically encoded data is generated by encoders 664, 674, 682, 686, 700 and 704 and completely specifies the location and orientation of probe instrument 656 relative to the person's jaw.

As illustrated in FIG. 33, bite block 692 comprises a plurality of off-the-shelf components 710 which are selected by the dental practitioner from a stock or inventory of bite block parts. The stock components 710 are incorporated into a settable plastic composition 712 which is formed or molded to a portion of the tooth and gum surfaces and allowed to harden. A preformed block 714 provided with reference slots 716 may be attached to bite block 692 for facilitating the calibration of articulated arm assembly 654 and establishing a reference frame or coordinate system relative to the jaw.

Universal joint 690 is fixed to bite block 692, preferably after the bite block has hardened on the patient's dentition. The inner end of arm segment 680 is attached to an inner race 718 of a first bearing 720. That first bearing 720 has an outer race 722 which is rigid with an inner race 724 of a second bearing 726. An outer race 728 of bearing 726 is in turn fixed to a platform 730 mounted to bite block 692.

In order to augment the accuracy of the contour data generating assembly, a plurality of strain gauges 732 and 734 are connected between bite block 692 and surfaces of the patient's teeth. Strain gauges 732 and 734 are electrically coupled via leads 736 and 738 to computer 24. Computer 24 is programmed to take into account incremental motions of bite block 692 relative to the patient's jaw when calculating the position and orientation of probe instrument 656.

Bite block 692 may be automatically fabricated by computer 24 using numerical control techniques and operating on data provided by the surface data generating assembly 22 (FIG. 1) and/or contour data generating assembly 26. In that event, computer 24 carves or machines bite block 692 from a blank of hard polymeric material or alternatively machines mold members which are used to cast the bite block. Computer 24 can select the shape and size of bite block 692, the place of attachment thereof to the patient's teeth and the location of universal joint 690 on bite block 692. Preformed sleeves (not shown) may be provided which are embedded in bite block 692, either manually or automatically unde the control of computer 24.

As further illustrated in FIG. 33, computer 24 has an output lead 740 extending to schematically represented locking mechanisms 742 for temporarily locking articulated arm assembly 654 to prevent motion thereof. More particularly, in response to a signal from computer 24, mechanisms 742 lock arm segment 668 and block 670 to arm segment 678, arm segments 678 and 680 to one another, and the various components of universal joint 690. The purpose of the locking function is described hereinafter with reference to FIGS. 36-39. Locking mechanisms 742 may be electromagnetic, hydraulic or pneumatic.

Figure 34:
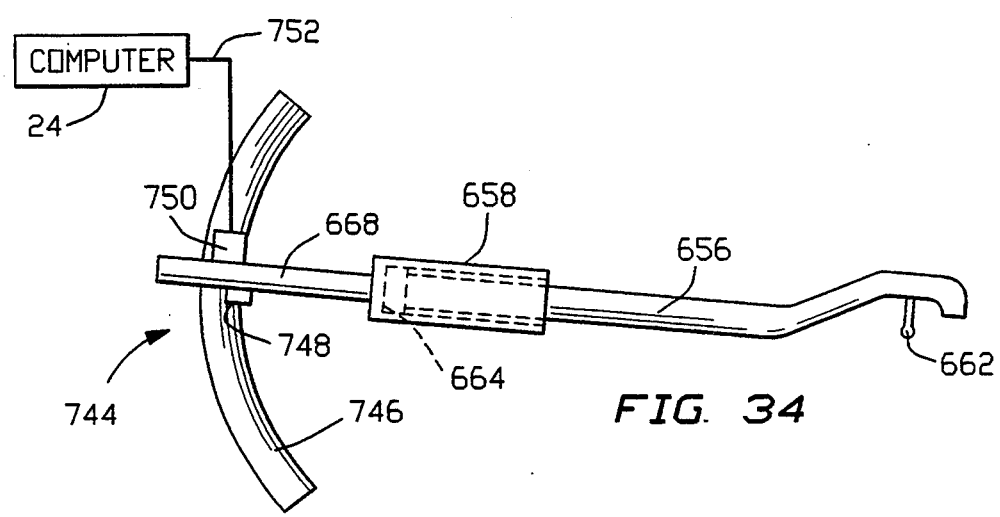
FIG. 34 is a schematic side elevational view of a modification of the surface data generating device of FIGS. 32 and 33.

As illustrated in FIG. 34, arm segment 668 may be connected to arm segment 680 (FIGS. 32 and 33) via a rotational coupling 744 including a track 746 in the form of a circular segment, a slider 748 for slidably connected arm segment 668 to track 746 and an encoder 750 similar to encoders 700 and 704 for detecting relative motion between arm 668 and slider 748, on the one hand, and track 746, on the other hand. Encoder 750 is connected via a lead 752 to computer 24 for transmitting thereto a signal encoding the rotational status of arm segment 668.

The modification in the structure of articulated arm assembly 654 illustrated in FIG. 34 facilitates a pivoting of probe instrument 656 about an axis passing perpendicularly through the plane of the drawing and through instrument tip 662. The modified structure of FIG. 34 facilitates the collection of data relating to such a motion.

Figure 35:
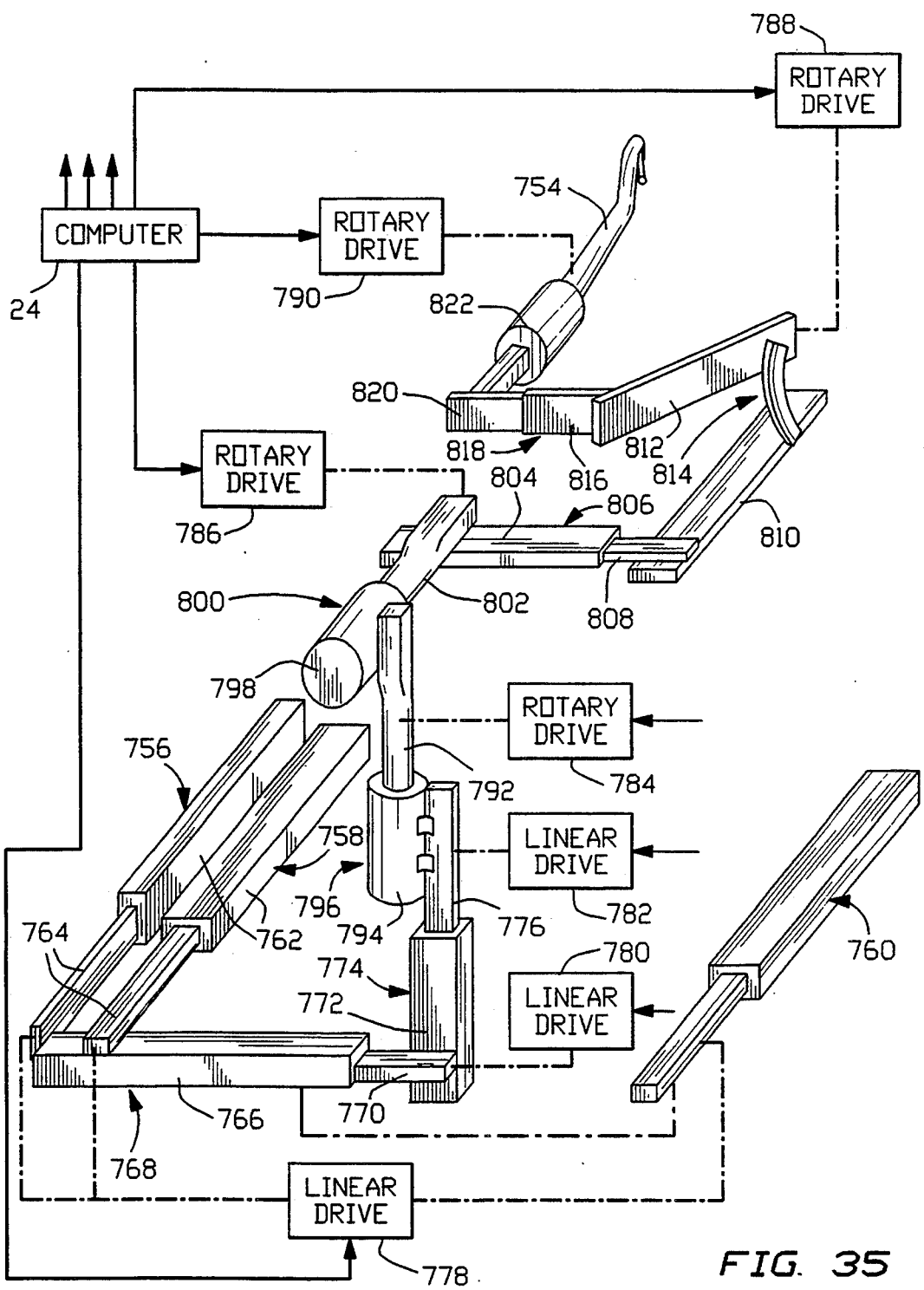
FIG. 35 is partially a block diagram and partially a schematic perspective view of a drill movement control assembly in accordance with the present invention.

FIG. 35 depicts a movement control assembly for automatically controlling the position and orientation of an operating instrument 754 relative to a patient's head and more particularly, relative to a jaw of the patient. The movement control assembly comprises a plurality of slider devices 756, 758, 760 each having a body member 762 which is fastened to the patient's jaw (e.g., via a bite block) prior to use of operating instrument 754. Each slider device 756, 758, and 760 further includes a slider rail 764 slidably mounted to the respective body member 762 and fixed to a body member 766 of at least one additional slider device 768.

Slider device 768 includes a slider rail 770 slidably mounted to body member 766 for linear motion in a direction substantially perpendicular to the direction of motion of slider rails 764 of slider devices 756, 758, and 760. Slider rail 770 is in turn rigid with a body member 772 of at least one additional slider device 774. Slider device 774 is oriented orthogonally to slider device 768, as well as slider devices 756, 758, and 760. A slider rail 776 of slider device 774 consequently shifts in a direction perpendicular to the directions of motion of slider rails 764 and 770.

Slider devices 756, 758, 760 and 768 and 774 enable complete control of the position of operating instrument 754 by computer 24. To that end, computer 24 is operatively connected to three linear drives 778, 780 and 782 which are in turn operatively coupled with slider rails 764, 770 and 776 for shifting those rails relative to their respective body members 762, 766 and 772. Linear drives 778, 780 and 782 may take any appropriate form such as rack and pinion, magnetic, electrical, etc.

In order to control the orientation of operating instrument 754 relative to the patient's head or jaw, computer 24 is operatively connected to four rotary drives 784, 786, 788, and 790. Rotary drive 784 is operatively linked to a rotating arm 792 for pivoting that arm about its longitudinal axis relative to a body member 794 of a first rotary device 796. Body member 794 is fastened to slider rail 776 of slider device 774.

Rotating arm 792 of rotary device 796 is rigid with a body member 798 of another rotary device 800. Rotary device 800 has a rotating arm 802 which is operatively coupled with rotary drive 786. Drive 786 serves to turn arm 802 about its longitudinal axis in response to signals from computer 24.

As further illustrated in FIG. 35, rotating arm 802 is attached to a body member 804 of a slider device 806 having slider rail 808 in turn attached to an elongate bar 810. A second elongate bar 812 is swingably attached to bar 810 via a rotary joint 814. Rotary drive 788 is operatively coupled with bar 812 for swinging that bar relative to bar 810.

Attached to a free end of bar 812 is the body member 816 of another slider device 818. Slider device 818 has a slider member 820 carrying a cradle 822 in which operating instrument 754 is disposed for rotation essentially about its longitudinal axis. Rotary drive 790 is operatively connected to operating instrument 754 for rotating that instrument about its axis under the control of computer 24.

Slider devices 806 and 818 are provided to facilitate the disposition of rotary joint 814 so that it is juxtaposed to the operating tip 755 of instrument 754. Rotary joint 814 is accordingly disposable, for example, between the buccal surfaces of molar teeth and a cheek of the patient. Slider devices 806 and 818 are provided with locking components (not illustrated) for fixing the dispositions of slider rails 808 and 820 relative to slider bodies 804 and 816. Of course, the structure of FIG. 35 may be simplified by omitting slider devices 806 and 818 and connecting rotary joint 814 more directly to rotating arm 802.

Operating instrument 754 may take the form of a dental drill, a surgeon's scalpel, a curette, etc. In each case, computer 24 is preprogrammed with a respective motion or set of motions for determining the position and orientation of operating instrument 754. Computer 24 is fed the motions via use of the contour data generating device of FIGS. 11, 14 or 32 and 33. A minor change in programming induces computer 24 to record an entire motion for later reproduction by the movement control assembly of FIG. 35 or of FIGS. 36-39, as discussed below.

In the case that operating instrument 754 is a drill, for example, a further drive (not illustrated) is provided for energizing the drilling operation.

It is to be noted that the various linear drives 778, 780, 782 and rotary drives 784, 786, 788 of the movement control assembly of FIG. 35 may be replaced with respective linear and rotary encoders, whereby the assembly is converted to a position recording assembly. Conversely, encoders 664, 674, 682, 686, 700, and 704 of the articulated arm assembly 654 of FIGS. 32 and 33 may be replaced by motors and respective drive transmission elements, whereby the articulated arm assembly is converted to a movement control or drive assembly.

Arm segment 668 in FIG. 32 and 33 may be replaced by an arm 824 having a U-shaped portion 826. The motion of arm 824 is monitored by encoder 674 (see also FIGS. 32 and 33). An instrument assembly 828 is removably attached to a free end 829 of U-shaped portion 826. Instrument assembly 828 includes a probe instrument 830 and a cradle 832 to which probe instrument 830 is mounted for rotation about a longitudinal instrument axis 834 passing through the operating tip 836 of the instrument. Cradle 832 carries a rotary encoder (not illustrated) for recording the angular position of instrument 830.

Figure 37:
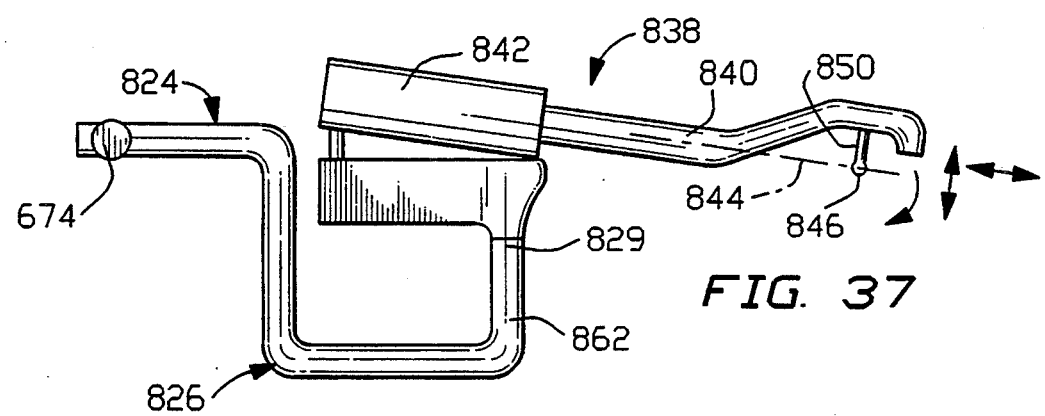
FIG. 37 is a schematic side elevational view of the modification of FIG. 36, showing the detachable probe unit replaced with a schematically illustrated movement control module.

FIG. 37 shows arm segment 824 with instrument assembly 828 replaced by a movement control assembly 838. Movement control assembly 838 includes a probe or operating instrument 840 and a cradle 842 to which instrument 840 is mounted for rotation about a longitudinal instrument axis 844 passing through the operating tip 846 of the instrument. Cradle 842 may carry a rotary drive (not illustrated) for determining the angular position of instrument 840.

Figure 38:
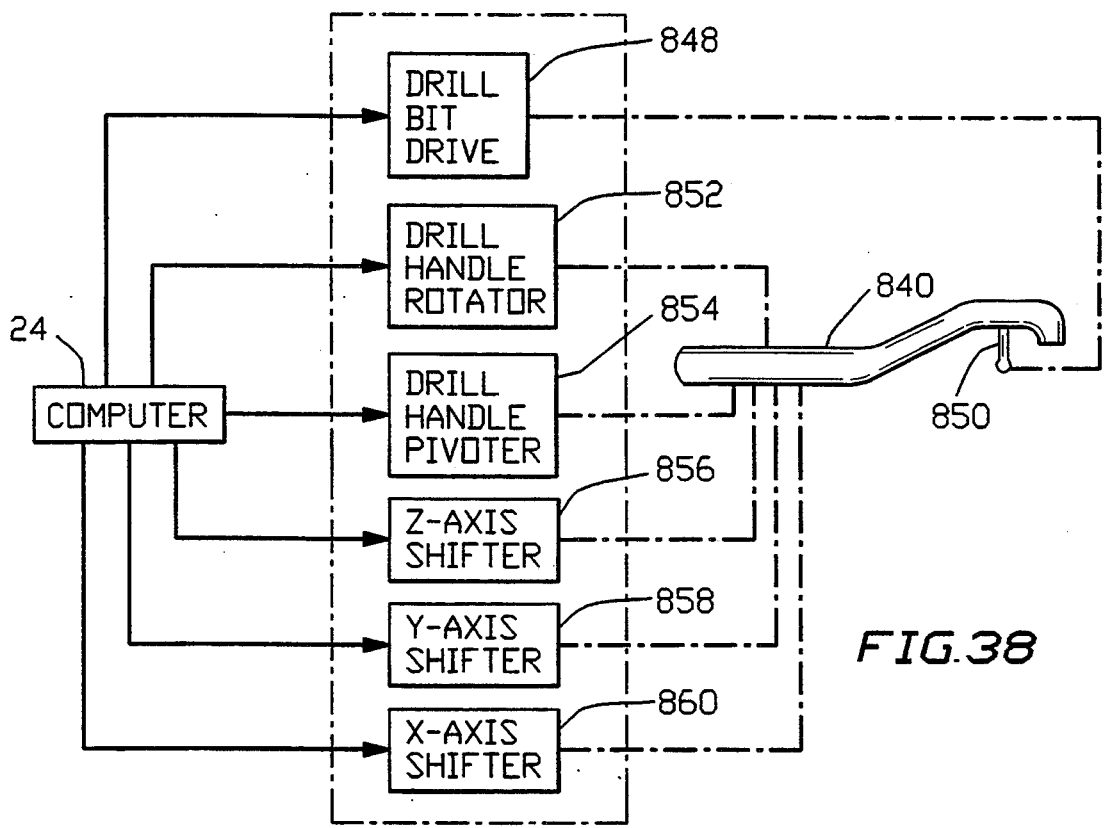
FIG. 38 is a block diagram illustrating functional components of the movement control module of FIG. 37.

As illustrated in FIG. 38, movement control assembly 838 includes a drill bit drive 848 for rotating the drill bit 850 about its axis, in the event that instrument 840 is a dental or surgical drill. Movement control assembly 838 further includes a handle rotator or drive 852 for rotating the operating instrument 840 about longitudinal axis 844 and a pivoting drive 854 for rolling instrument 840 about an axis perpendicular to the plane of the drawing sheet and passing through operating tip 846. Three linear drive 856, 858 and 860 are included in movement control assembly 838 for shifting instrument 840 along a x axis, a y axis and an x axis, respectively.

Computer 24 is operatively linked to drives 852, 854, 856, 858, and 860, as well as to drill bit drive 848, for coordinating the activation of those drives to reproduce an incremental type motion appropriate to instrument 840. It is to be noted in this regard that instrument 840 may take virtually any conventional form. For example, instrument 840 may be a curette, a scalpel or an image acquisition component similar to optical data generating device or assembly 26 (FIG. 1). In each case, the motion produced by movement control assembly 838 under the control of computer 24 is incremental with respect to a point determined by the orientations of arms 680, 678 (FIGS. 32 and 33) and 824 (FIG. 37).

Figure 36:
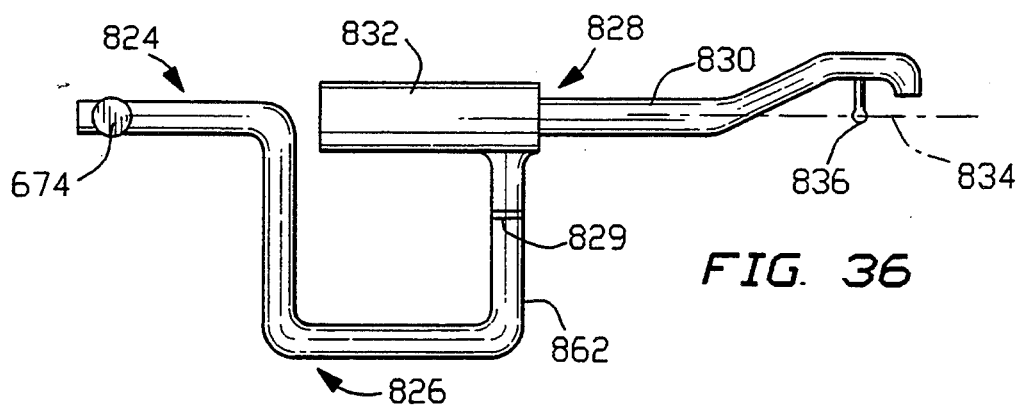
FIG. 36 is a schematic side elevational view of a modification of the surface data generating device of FIG. 32, showing a detachable probe unit.

In use, the dentist or surgeon holds articulated arm assembly 654 (FIGS. 32 and 33) in part along a rising shaft 862 of U-shaped portion 826 (FIG. 36). Upon determining that a tooth or bone surface is to be modified, the dentist or surgeon induces computer 24 to energize locking mechanisms 742 (FIG. 33), thereby maintaining the arm segments 824, 678 and 680 of articulated arm assembly 654 in position. The dentist or surgeon then removes probe instrument assembly 828 (FIG. 36) with one hand while continuing to hold shaft 862 with the other hand. Movement control assembly 838 with an appropriate instrument 840 is subsequently attached to the free end 829 of U-shaped portion 826.

In the event that instrument 840 is an optical or image acquisition component, lenses (not shown) are mounted to the distal end of the instrument and are rotated by handle rotator or drive 852 about longitudinal axis 844 and by pivoting drive 854 about an axis perpendicular to the plane of the drawing sheet and passing through operating tip 846.

In an advantageous method of collecting three-dimensional surface data where instrument 840 is an optical or image acquisition component, a multiple stylus contour probe (FIGS. 18-23), an interferometer device, a gray level sensor, etc., a single stylus probe such as data generating device or assembly 26 (FIG. 1) or the assembly of FIGS. 32 and 33 is first used to define boundaries of a given structure in the mouth. The electrical signals defining the boundaries are transmitted to computer 24. Upon the definition of the boundary, surface data collecting instrument 840 is attached to shaft 862 of U-shaped articulated assembly portion 826, along with movement control assembly 838, while the U-shaped portion is held by the operator at a first reference position, for example, opposite an occlusal surface of a tooth structure. Control assembly 838 is then operated by computer 24 (pursuant to instructions from the dentist) to move data collecting instrument 840 according to a preprogrammed path, the incoming data being automatically fed to computer 24. Upon the termination of a first data collection sweep, the user may manually move the articulated arm assembly (FIGS. 32, 33, 36, 37) to place U-shaped portion 826, movement control assembly 838, and accordingly instrument 840 at a second reference position, for example, opposite a buccal surface of the tooth structure. Control assembly 838 is again operated by computer 24 to move data collecting instrument 840 according to a preprogrammed path, the incoming data being automatically fed to computer 24. This semi-automated procedure may be repeated as many times as necessary to define the structure outlined by the boundary defining step at the commencement of the data collection operation. At the termination of the data collection operation, a manually moved probe on an articulated arm assembly (e.g., the assembly of FIGS. 32, 33 and 36, 37) may be used to "fill in" the three-dimensional surface data at any areas where the data is weak or lacking.

Instead of the dentist instructing the computer as to the new location, for example, by pressing a keyboard button upon placement of the control assembly 838 and instrument 840 at a new reference position, the computer may instruct the user as to the reference position which is required. This instruction may be implemented by voice synthesis and/or a read-out on a monitor. Similarly, instructions from the operator to computer 24 may be implemented via voice recognition.

Figure 39:
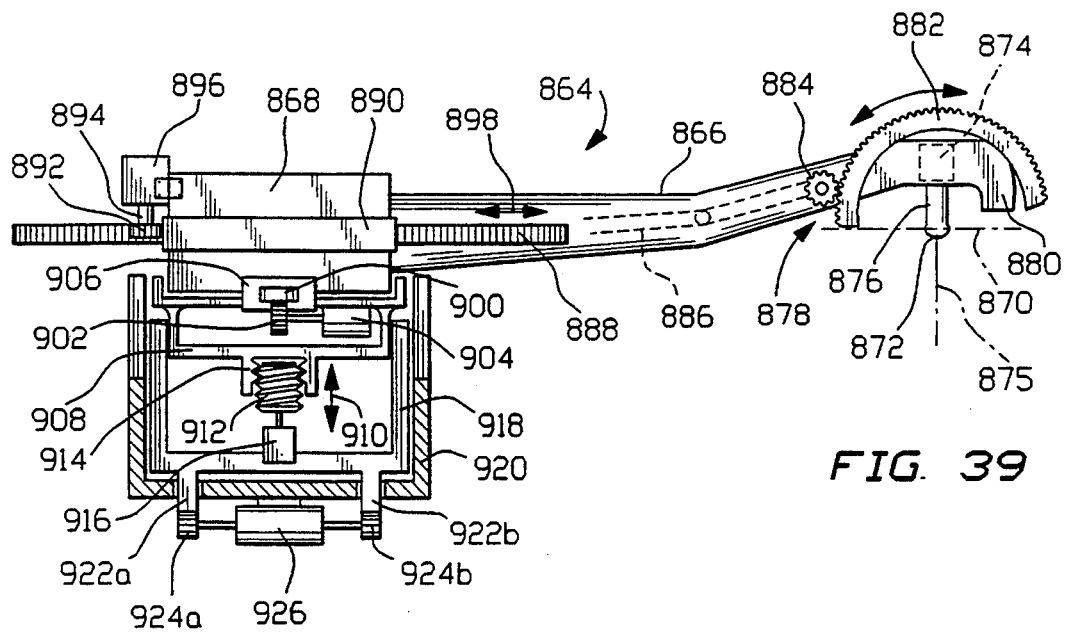
FIG. 39 is a side elevational view of a particular embodiment of the movement control module of FIG. 37.

FIG. 39 illustrates a particular embodiment of a movement control assembly 864 which may be temporarily attached to U-shaped articulated arm assembly portion 826. Movement control assembly 864 includes a probe or operating instrument 866 and a cradle 868 to which instrument 866 is mounted for rotation about a longitudinal instrument axis 870 passing through the operating tip 872 of the instrument. Cradle 868 may carry a rotary drive (not illustrated) for determining the angular position of instrument 866.

As further illustrated in FIG. 39, movement control assembly 864 includes a conventional pneumatic drill bit drive 874 for rotating drill bit 876 about its axis 875, in the event that instrument 866 is a dental or surgical drill. Movement control assembly 864 also includes a rotator drive 878 for rotating an operating instrument head 880 about an axis extending perpendicularly to axes 870 and 875. Rotator drive 878 comprises, for example, an arcuate rack 882 meshingly engaged by a pinion 884 in turn driven via a shaft 886 extending through instrument 866 from cradle 868.

Connected to instrument 866 is at least one linear rack 888 translatably mounted to cradle 868 via a sleeve 890. Rack 888 meshingly engages a pinion 892 mounted to an output shaft 894 of a rotary motor 896 mounted to cradle 868. Rotary motor 896 drives rack 888 and consequently reciprocates instrument 866 along axis 870, as indicated by an arrow 898.

Cradle 868 is translated in a direction perpendicular to axes 870 and 875, i.e., in a direction perpendicular to the plane of the drawing, via a rack 900 rigid with cradle 868 and a pinion 902 driven by a rotary motor 904. Rack 900 is shiftably mounted to a collar 906 in turn rigid with a frame member 908 to which rotary motor 904 is fastened. Frame member 908 is shifted in a vertical direction (see arrow 910) via a worm screw 912 threadingly engaging a collar 914 integral with frame member 908. Screw 912 is rotated by a drive 916 attached to a carriage 918 which can be rotated, together with frame member 908 and cradle 868, about axis 870. Carriage 918 is slidably mounted to a holder 920 and is driven by a pair of racks 922a and 922b meshing with respective pinions 924a and 924b connected to a rotary motor 926 mounted to holder 920.

Figure 40:
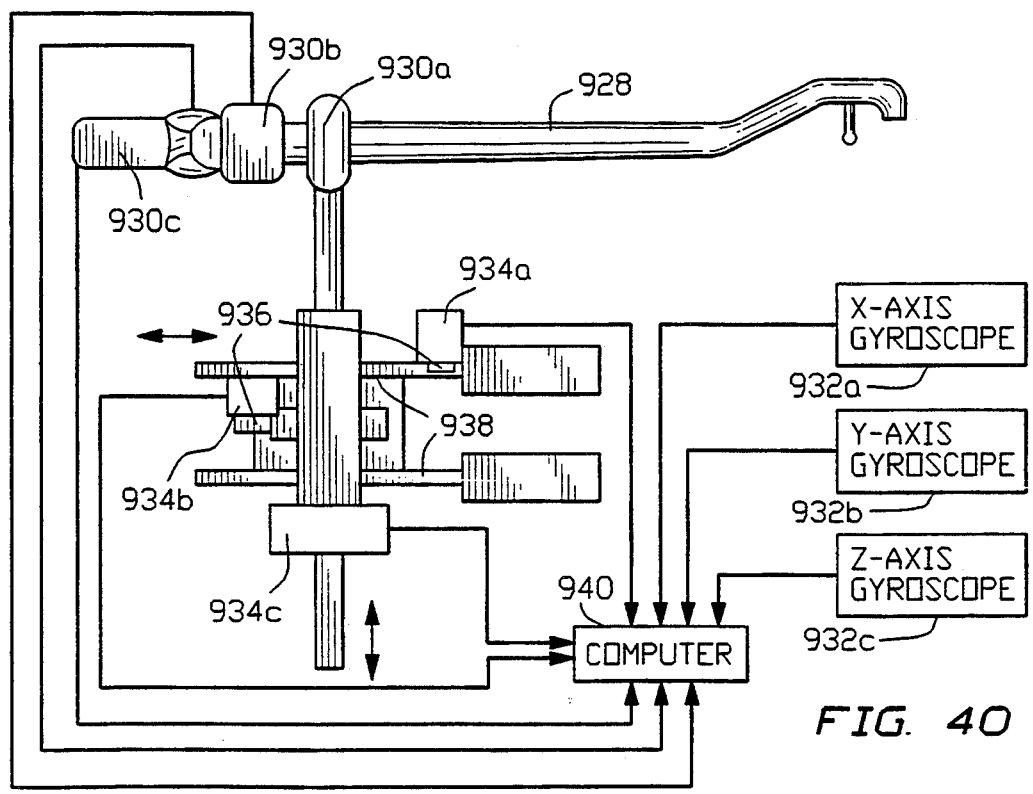
FIG. 40 is partially a block diagram and partially a schematic side elevational view of a further surface data generating device in accordance with the present invention.

As illustrated in FIG. 40, a device for use in a dental or medical application to obtain three-dimensional contour information comprises a hand held dental instrument 928 and a plurality of gyroscope components 930a, 930b, and 930c each generating an electrical output signal indicative of the orientation of the respective gyroscope component. Gyroscope components 930a, 930b, and 930c are mechanically connected to dental instrument 928 to provide electrical output signals indicative of the orientation of the dental instrument. A plurality of additional gyroscope components 932a, 932b, and 932c are mechanically connect to a patient's jaw to provide electrical output signals indicative of the orientation of the jaw. Three signal generators 934a, 934b, and 934c are mechanically coupled to dental instrument 928 for example, via respective pinions 936 and racks 938 and to the patient's jaw for producing electrical output signals indicative of the translatory position of the dental instrument relative to the jaw. A computer 940 is operatively connected to gyroscope components 930a, 930b, 930c and 932a, 932b, and 932c and signal generators 934a, 934b, and 934c for receiving the electrical output signals thereof and for computing the position and orientation of the dental instrument relation to the jaw.

The device of FIG. 40 represents a means for obtaining three-dimensional contour information which is an alternative to the probes and optical instruments described herein.

Figure 41:
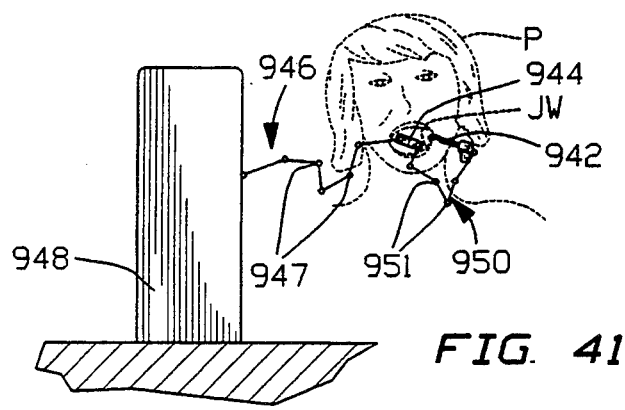
FIG. 41 is a diagram of another surface data generating and/or operating system in accordance with the present invention.

FIG. 41 schematically illustrates another alternative system for obtaining three-dimensional contour and surface data from a patient P and/or for operating on the patient. The system of FIG. 41 serves to track position and orientation of a probe or operating instrument 942 relative to a body part of the patient, such as the patient's jaw JW. A reference element 944 such as a bite block is fixed to jaw JW, while a first articulated arm assembly 946 is connected on the one side to a stationary fixture 948 and on the other side to the bite block reference element 944. A second articulated arm assembly 950 is connected to bite block 944 and to probe or operating instrument 942. It is to be noted that second articulated arm assembly 950 may take the form illustrated and described hereinabove with reference to FIGS. 32, 33 and 36, 37.

Articulated arm assembly 946 is provided with encoders 947 and a first feedback mechanism and/or circuit 952 (see FIG. 44) for providing electrical signal feedback data as to position of and orientation of bite block 944 relative to stationary fixture 948. Articulated arm assembly 950 is similarly provided with encoders 951 and a feedback mechanism and/or circuit (not shown in FIG. 41) for providing electrical signal feedback data as to position of and orientation of instrument 942 relative to bite block 944.

Accordingly, it is to be understood that the dual arm system of FIG. 41 is capable of providing accurate digitized contour and surface information and can be used as an alternative to the other contour and surface date generating or collecting system described herein.

Figure 42:
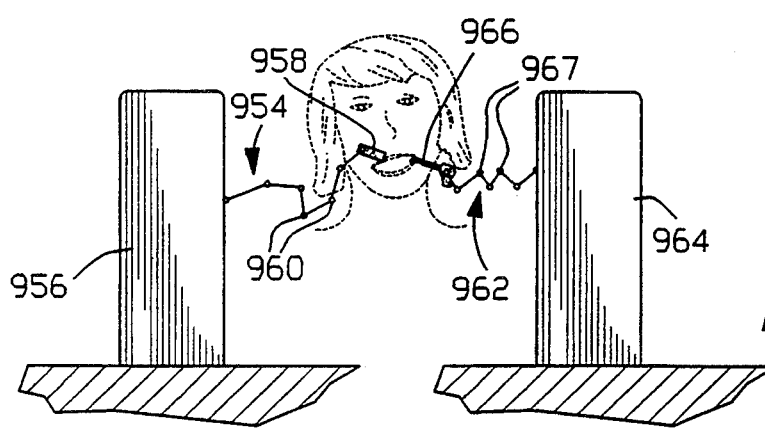
FIG. 42 is a diagram of yet another surface data generating and/or operating system in accordance with the present invention.

FIG. 42 illustrates yet another contour and/or surface data gathering system and comprises a first articulated arm assembly 954 connected at a base end to a first stationary fixture 956 and at an opposite end to a reference element 958, for example, a bite block. Arm assembly 954 includes encoders 960 for producing electrical output signals indicative of the position and the orientation of bite block reference element 958. A second articulated arm assembly 962 is similarly coupled at a base end to a second stationary fixture 964 and at an opposite end to a probe or operating instrument 966. Articulated arm assembly 962 bears encoders 967 which provide electrical feedback to a computer (e.g., computer 24). With the data from encoders 960 and 967, the computer can generate an accurate electronic model of a structure to which reference element 958 is firmly connected and which is scanned by probe 966.

Figure 43:
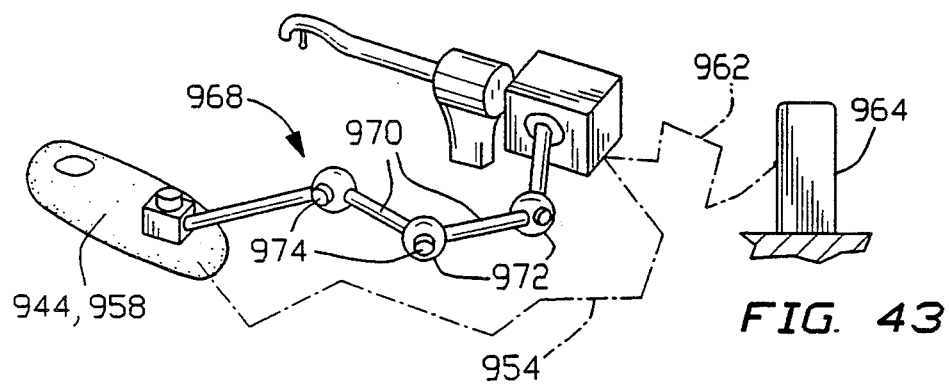
FIG. 43 is a schematic perspective view of a locking mechanism, in accordance with the present invention, for use with the surface data generating and/or operating systems of FIGS. 41 and 42, upon attachment of a motorized instrument movement control assembly to those systems.

It is to be noted, in congruence with other embodiments described herein, that the instrument-bearing articulated arm assemblies 950 and 962 of FIGS. 41 and 42 may take the form of motorized assemblies, such as that illustrated in FIG. 35. Alternatively, arm assemblies 950 and 962 may be provided with detachable motorized movement control assemblies such as those described above with reference to FIGS. 36–39. Upon attaching such a movement control assembly to articulated arm assembly 950 or 962, the movement control assembly may be temporarily fixed to the patient by connecting, to reference element 944 or 958 and to the movement control assembly, another articulated assembly 968 schematically illustrated in FIG. 43. Articulated assembly 968 includes a plurality of arm segments 970 connected to one another via universal joints 972. Upon a disposition of the probe or operating instrument 942 or 966 at a desired location, joints 972 are locked by actuating mechanical or pneumatic locking mechanisms 974 connected to the joints 972. Alternatively, a rigid bracket (not illustrated) may be connected to the movement control assembly and held to the patient manually.

Figure 44:
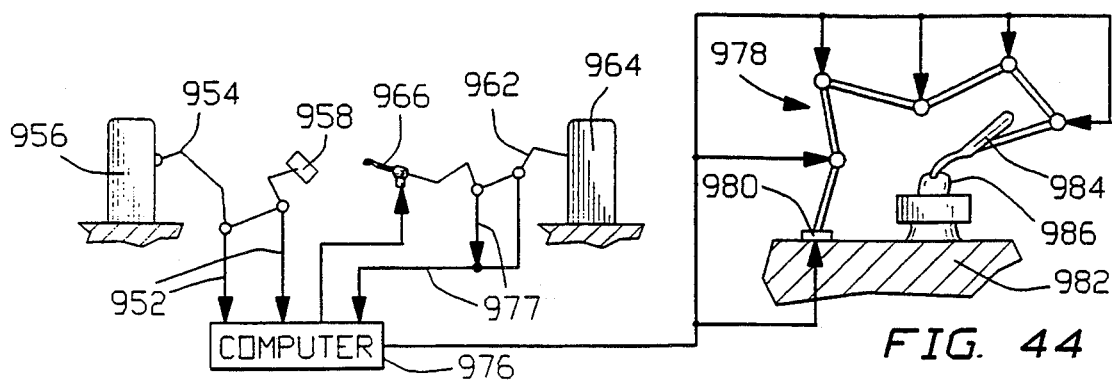
FIG. 44 is partially a block diagram and partially a schematic of a system for modifying a pre-existing structure by operating first on a model of the structure, in accordance with the present invention.

As depicted in FIG. 44, a computer 976 receiving position feedback signals from encoders 960 and 967 of articulated arm assemblies 954 and 962 (or 946 and 950) via circuits 952 and 977, respectively, is operatively connected to a motorized articulated arm assembly 978 which is mounted at 980 to a work bench 982. Articulated assembly 978 may have a structure similar to the motorized assembly of FIG. 35 or may alternatively be identical to articulated assembly 962, with encoders being replaced by rotary motors.

The system depicted in FIG. 44 is useful in an integrated procedure for producing a prosthetic dental appliance and preparing tooth, bone and/or gum structures in a patient's mouth for receiving the dental appliance. As described hereinabove with reference to the system of FIG. 1, computer 976 generates on a monitor (e.g., monitor 34 in FIG. 1) a graphic representation of external and/or internal structures in the patient's mouth. Computer 976 may then be operated to generate on the monitor screen a graphic representation of a proposed dental preparation and/or a prosthetic appliance to be attached to the preparation. The dental practitioner may interact with computer 976 to modify the electronically encoded preparation and/or appliance. As further discussed hereinabove, the dental practitioner may operate a virtual operating instrument and thereby practice a selected surgical operation, the operation being monitored by computer 976 via articulated arm assemblies 954 and 962. Computer 976 illustrates the operations on the monitor, thereby providing immediate visual feedback to the practitioner as to the predicted effects of his movements.

For a contemplated surgical procedure, computer 976 may also recommend to the dentist a surgical instrument, for example, a size and type of burr, as well as show on the computer monitor a recommended manner of holding the instrument and of moving it to perform the contemplated procedure.

Upon the attainment of a desired surgical motion, computer 976 generates signals to actuate motorized arm assembly 978 to move a dental instrument 984 in conformity with the desired surgical motion. Dental instrument 984 is operated to act upon a model 986 of the tooth, bone and/or gum structures in the patient's mouth which are to receive a dental appliance. Arm assembly 978 moves dental instrument 984 in a manner identical to that previously practiced and approved by the practitioner. The practitioner is thereby provided with an additional learning and/or approval opportunity. By watching the motions of instrument 984, the dentist obtains further information with which to perform the operation on the actual tooth, bone and/or gum structures in the patient's mouth. Alternatively, once the preparation is approved, the operation on the actual tooth, bone and/or gum structures may be implemented automatically by computer 976 which transmits signals controlling a motorized movement control module (e.g., FIGS. 36–39) on arm assembly 962 or a motorized arm assembly (FIG. 35). Computer 976 controls the movement control module or the motorized arm assembly in accordance with electrical signals encoding the approved motion, as shown on the computer monitor and/or as actually performed on model 986 by arm assembly 978.

Computer 976 may also use arm assembly 978 to machine a prosthetic dental appliance in accordance with the specifications as shown on the computer monitor and as approved by the dentist. Alternatively, the dental appliance may be produced at a laboratory to which the electrical codification of the appliance is sent via modem or disk. In any event, the prosthetic appliance may be finished and in the dentist's hands prior any preparation work on the patient's teeth or bone.

This method is particularly beneficial for implant operations. The type, size and angular configuration of an implant anchor or blade, as well as the contours of a crown, bridge, splint or other prosthesis to be attached to the anchor, are all calculated before any preparation is undertaken on the patient's dentition. The location and orientation of the implant blade or anchor are selected as described above with reference to FIGS. 25–31. Prior to preparation work, the prosthesis is produced in accordance with an electronic model generated through interaction between computer 976 and the dentist. As described in detail hereinabove, the electronic model is based on contour and surface data as to external tooth and gum structures and internal data as to tooth and bone structures. The internal data is received from X-ray, panoramic X-ray and/or computer tomographic devices, as is conventionally known in the art. Computer 976 combines the internal data with the contour and surface data as to the external structures, as described above with reference to FIGS. 25–31. Upon receiving the data as to internal and external surfaces and instructions as to the operations and prostheses desired, computer 976 may provide the user with recommendations as to location and orientation of implant blades and the surface configurations of prosthetic elements. These recommendations may include operative techniques and instrument motions which have been programmed into computer 976 in accordance with the techniques of recognized experts in the field. Programming of recommended instrument motions is implemented simply by having the individual expert operate on a patient or a model using any of the articulated arm or data gathering assemblies described herein. Computer 976 (or another, central computer) records the positions and orientations of the instrument during the entire procedure. Of course, the individual dentist may modify the recommendations in accordance with their own experience and any further information available in the particular situation.

Figure 45:
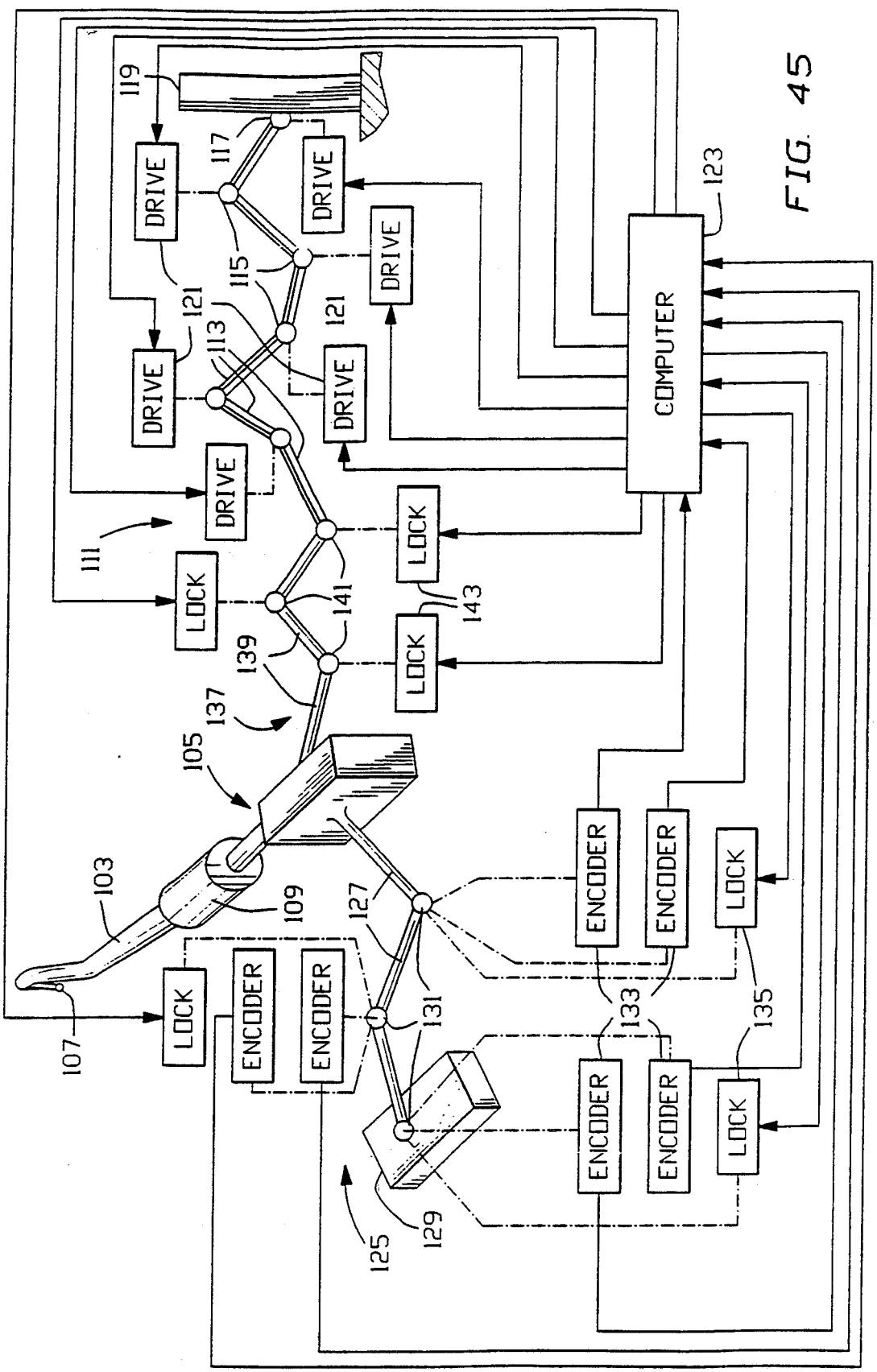
FIG. 45 is partially a block diagram and partially a schematic of a system for modifying a pre-existing structure, in accordance with the present invention.

FIG. 45 illustrates yet another automated system for implementing a surgical operation on a patient, for example, on a tooth or jaw bone structure. A surgical instrument 103 is mounted to a movement control or drive assembly 105 which may take a form described hereinabove with reference to FIGS. 36–39. Movement control or drive assembly 105 is operatively coupled to instrument 103 for incrementally moving the instrument about a reference point, for example, at the operating tip 107 of instrument 103 or another point 109. A second movement control or drive assembly 111 is operatively coupled to instrument 103 for shifting the reference point 107 or 109, for example, along a predetermined path within a predefined bounded region.

In the embodiment illustrated schematically in FIG. 45, movement control or drive assembly 111 includes three to six articulated arms 113 connected at rotary joints 115 to each other. At a base end 117, articulated movement control or drive assembly 111 is secured to a stationary fixture 119. A plurality of rotary drive motors 121 are operatively linked to arms 113 and/or joints 115 to move the arms relative to one another in accordance with a preprogrammed motion stored in a computer 123 electrically or otherwise connected to drive motors 121. Movement control or drive assembly 111 may more specifically take the form of any six-axis robot arm disclosed herein (e.g., FIG. 35), including any six-axis data gathering articulated arm assembly described herein, with encoders being replaced by motors. Movement control or drive assembly 111 may have only three arms 113 connected by univeral joints 115.

A detector in the form of an articulated arm assembly 125 is operatively coupled to instrument 103 for monitoring position and orientation thereof. Articulated arm assembly 125 includes three arm segments 127 connected to each other and to a fixture 129 by universal joints 131 (see universal joint 690 in FIG. 33). Fixture 131 may take the particular form of a bite block, in the event that instrument 103 is a dental instrument or is otherwise designed for operating on a person's head regions. Alternatively, fixture 131 may be stationary, in which case an additional detector, for example, in the form of an articulated arm assembly connected between a stationary fixture and the patient's jaw, may be needed for keeping track of motions of the head or jaw.

Articulated arm assembly 125 incorporates feedback device(s), for example, in the form of rotary encoders 133, operatively coupled with at least some arm segments 127 for providing electrical signal feedback data as to positions of the arm segments relative to one another, thereby providing information as to position and orientation of movement control or drive assembly 105 and therefore of instrument 103. To that end, a distal end of articulated arm assembly 125 is coupled to movement control or drive assembly 105.

Articulated arm assembly 125 is further provided with a plurality of pneumatic, hydraulic, or electromagnetic locking mechanisms 135 for locking arm segments 127 relative to one another to rigidify articulated arm assembly 125. Locking mechanisms 135 thus ensure that reference point 107 or 109 is fixed in space relative to a patient. As described hereinabove with reference to FIGS. 36–39, movement control or drive assembly 105 incrementally moves instrument 103 about reference point 107 or 109.

It is to be noted that articulated arm assembly 125 may alternatively take the form of any six-axis data generating device disclosed herein (e.g., FIGS. 32 and 33), including any six-axis data gathering articulated arm assembly.

Another articulated assembly 137 is coupled at one end to movement control or drive assembly 111 and at an opposite end to movement control or drive assembly 105. Articulated assembly 137 includes three arm segments 139 connected to one another and to either movement control assembly 111 or movement control assembly 105 via universal joints 141. Pneumatic, hydraulic, or electromagnetic locking mechanisms 143 are operatively connected to arm segments 139 and/or joints 141 for locking the arm segments relative to one another to rigidify articulated arm assembly 137 in the event that movement control or drive assembly 111 is actuated by computer 123 to move reference point 107 (or 109). Thus, when the reference point of movement control or drive assembly 105 is being adjusted by movement control or drive assembly 111, locking mechanisms 143 are energized to rigidify articulated arm assembly 137 and locking mechanisms 135 are deactivated to ensure that articulated arm assembly 125 is freely movable. During a shifting of movement control or drive assembly 105 and instrument 103 by movement control or drive assembly 111, encoders 133 provide to computer 123 encoded feedback as to the position and orientation of movement control or drive assembly 105 and instrument 103 relative to fixture or bite block 131.

As described hereinabove with reference to FIGS. 36-39, it will be understood that computer 123 operates movement control or drive assembly 105 to implement previously stored motions which have been recorded via the use of an articulated arm assembly or pantographic monitor according to embodiments thereof presented herein. In addition, the adjustment of reference point 107 is according to a preprogrammed path or agenda, depending on the particular type of operation which is being executed. A microsurgical operation on brain tissue thus involves different movements than a bone drilling operation in preparation for a dental implant. In either case, the particular programmed motions may be practiced previously in virtual operations and reviewed, modified, and accepted by the surgeon or dentist prior to any actual cutting of the patient, as described hereinabove, for example, with reference to dental implants.

Figure 46:
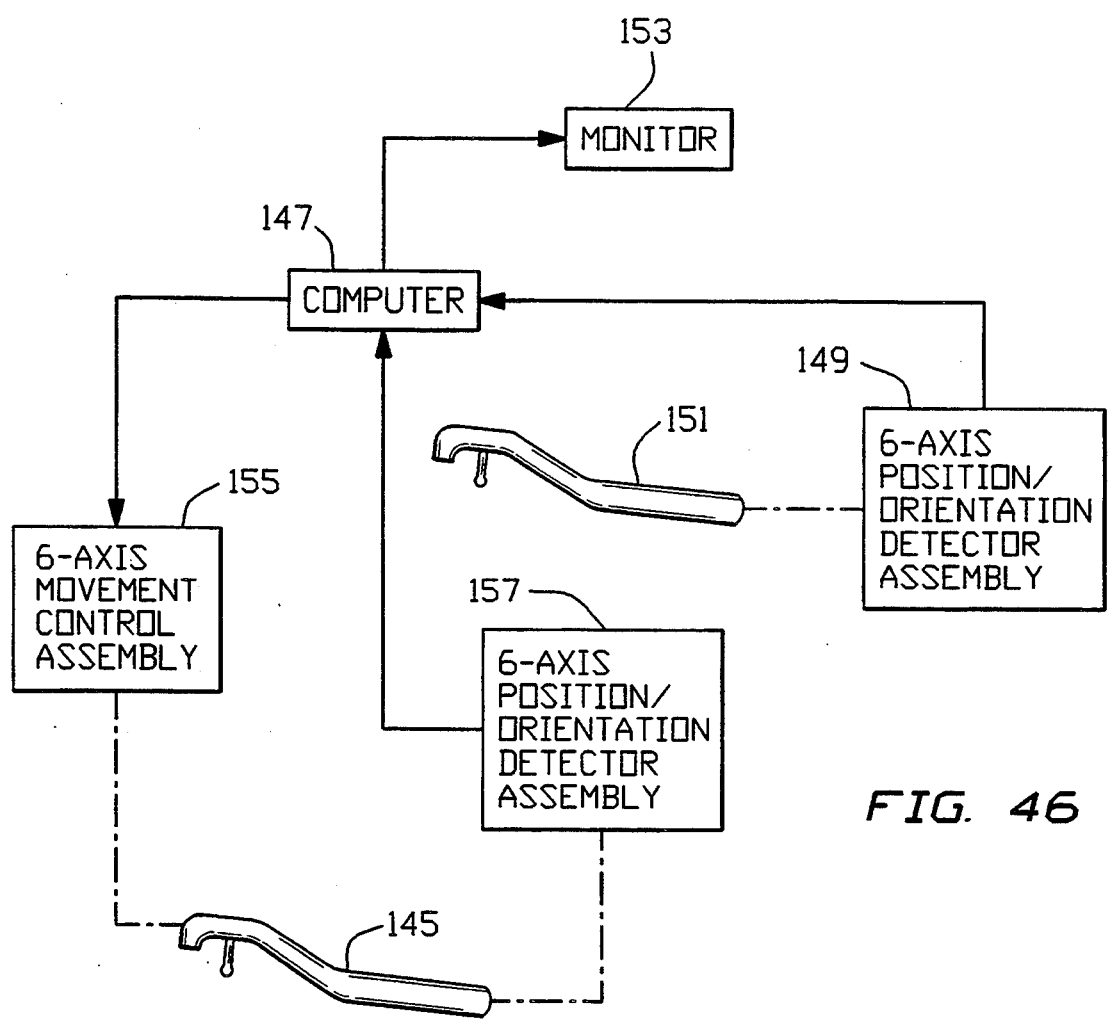
FIG. 46 is partially a block diagram and partially a schematic of another system for modifying a pre-existing structure particularly for small or minute structures, in accordance with the present invention.

As depicted schematically in FIG. 46, a system for per-forming fine and delicate surgical operations, for example, with an operating tool 145, comprises a computer 147 receiving position and orientation encoding signals from a six-axis detector assembly 149. It is to be noted that six-axis detector assembly 149 may take the form of any six-axis data generating device disclosed herein (e.g., FIGS. 32 and 33), including any six-axis data gathering articulated arm assembly.

As further depicted in FIG. 46, six-axis position and orientation detector assembly 149 is connected to a manipulable member 151 preferably identical to surgical instrument or operating tool 145. A surgeon or dentist manipulates member 145 while watching a monitor 153 on which computer 147 displays the position and orientation of operating tool 145 in relation to a graphically represented structure on which the operation is to be ultimately performed. The surgeon watches the screen until he or she is satisfied as the accuracy or the surgical motions. Computer 147 is then instructed to memorize the motion for future reptition on a reduced scale appropriate to the actual structure on which the operation is to be performed. Computer 147 controls a six-axis movement control or drive assembly 155 which is operatively coupled to operating tool 145 for moving the tool according to the memorized motion and on a reduced scale programmed into the computer previously. Six-axis detector assembly 149, computer 147, and six-axis movement control or drive assembly 155 thus cooperatively function as a motion reduction device operatively coupled to manipulable member 151 and surgical tool 145 for controlling motion of the tool to reproduce motions of the manipulable member on a reduced scale. This system is ideal for performing fine and delicate operations on sensitive tissues such as jaw bones and brain tissues. The motions made by the surgeon or dentist on manipulable member 151 while sitting at a work bench or table (not shown) are large scale and easily within the normal range of hand manipulations. In addition, monitor 153 may provide, on an enlarged scale, images of the tissues to be surgically modified or removed and the actual instrument or tool 145 which will perform the surgery.

Another six-axis detector assembly 157 as described herein is operatively connected to operating tool 145 for providing position and orientation feedback data to computer 147. In addition, in the event that the patient is not fixed, another detector assembly (not shown) may be connected to the patient, as described herein, for continuously and instantaneously monitoring the position and orientation of the patient or any body part of the patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

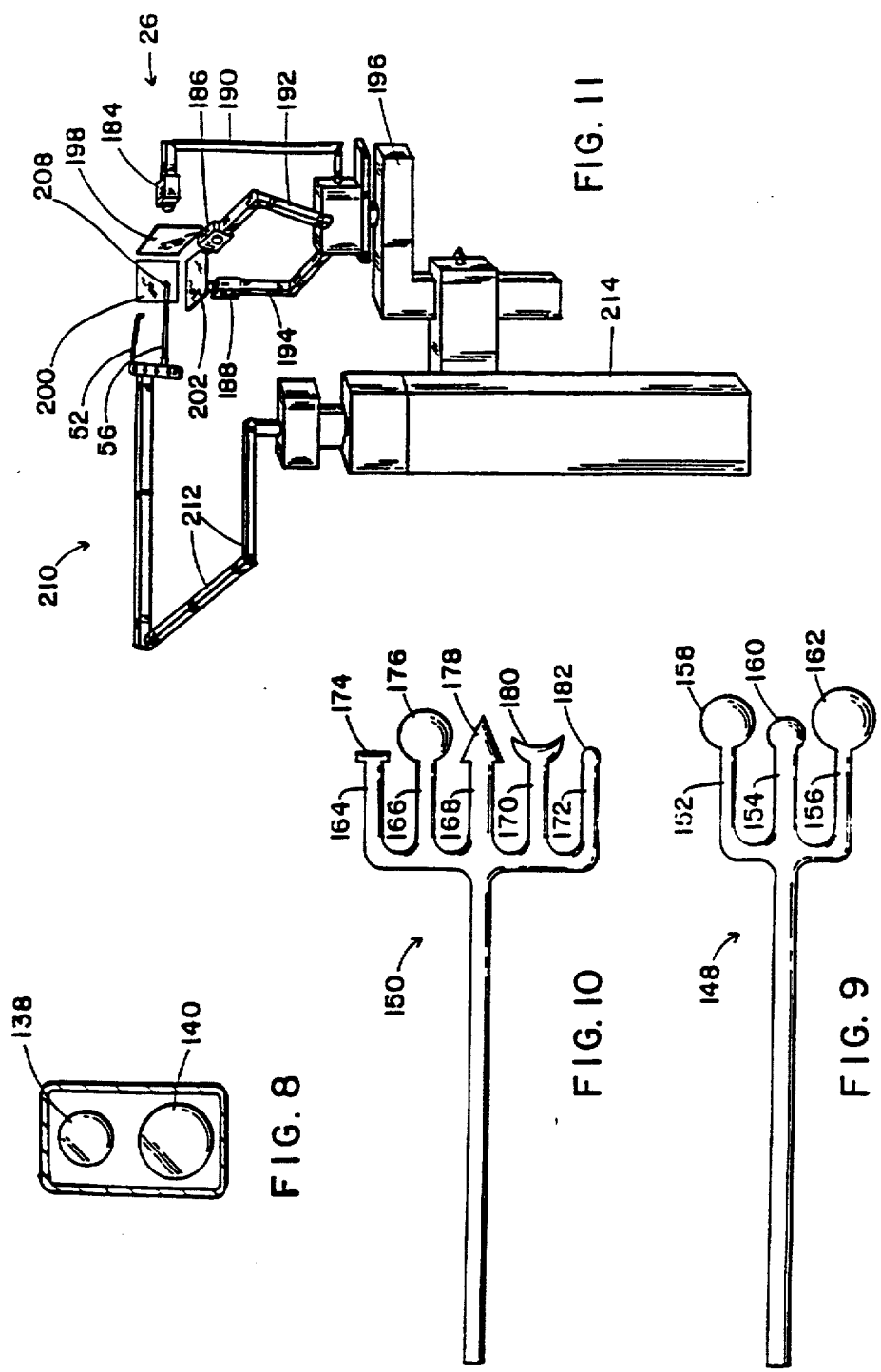

What is claimed is:

1. A device for use in a dental or medical application to obtain three-dimensional contour information, comprising:
   a multiplicity of arm segments;
   first mounting means for connecting said arm segments to one another to form an articulated assembly of said arm segments;
   second mounting means for fixing said articulated assembly relative to a person's head;
   third mounting means for attaching a diagnostic or medical treatment instrument to said articulated assembly at a point spaced from said second mounting means; and
   feedback means operatively coupled with at least some of said arm segments for providing electrical signal feedback data as to positions of said arm segments relative to one another, thereby providing information as to the position of said instrument relative to the person's head.

2. The device defined in claim 1 wherein said second mounting means takes the form of a bite block for mounting said articulated assembly to a jaw of the person.

3. The device defined in claim 2 wherein said bite block includes reference means for establishing a coordinate system origin relative to said bite block.

4. The device defined in claim 3 wherein said reference means includes at least one landmark structure on said bite block.

5. The device defined in claim 2 wherein said bite block includes a plurality of stock pieces and means for fitting said stock pieces to the person's jaw.

6. The device defined in claim 2, further comprising means operatively connected to said bite block and to the patient's jaw for monitoring incremental motions of said bite block relative to the jaw.

7. The device defined in claim 1, further drive means mounted to said articulated assembly and operatively connected to said instrument for incrementally moving said instrument about a point determined by the configuration of said articulated assembly.

8. The device defined in claim 7 wherein said point constitutes an operating tip of said instrument.

9. The device defined in claim 7, further comprising fourth mounting means for removably mounting said drive means to said articulated assembly.

10. The device defined in claim 7, further comprising computer control means operatively linked to said drive means for energizing same.

11. The device defined in claim 7, further comprising locking means operatively connected to said articulated assembly for temporarily locking said arm segments relative to one another to thereby fix the location of said point relative to the patient.

12. The device defined in claim 1, further comprising means operatively connected to said second mounting means and to the patient's head for monitoring incremental motions of said second mounting means relative to the person's head.

13. The device defined in claim 12, further comprising means for connecting said means for monitoring and said feedback means to a computer, whereby said computer can precisely determine position and orientation of said instrument relative to the person's head.

14. The device defined in claim 1 wherein said feedback means includes a plurality of digital encoders.

15. The device defined in claim 1 wherein said feedback means includes a plurality of linear motion encoders.

16. The device defined in claim 1 wherein said feedback means includes a plurality of rotary encoders.

17. The device defined in claim 1 wherein said feedback means includes a plurality of gyroscopic elements.

18. A device for use in operating on a patient, comprising:
a multiplicity of arm segments;
first mounting means for connecting said arm segments to one another to form an articulated assembly of said arm segments;
second mounting means for fixing said articulated assembly relative to a person's head;
third mounting means for attaching an operating instrument to said articulated assembly at a point spaced from said second mounting means; and
drive means operatively coupled with at least some of said arm segments for controlling and modifying positions of said arm segments relative to one another, thereby determining the position and orientation of said instrument relative to the person's head.

19. The device defined in claim 18, further comprising computer control means operatively linked to said drive means for energizing same.

20. The device defined in claim 19, further comprising feedback means operatively coupled with at least some of said arm segments and with said computer control means for providing thereto electrical signal feedback data as to positions of said arm segments relative to one another, thereby informing said computer control means as to the position of said operating instrument relative to the person's head.

21. A device for use in a dental/medical application to obtain three-dimensional contour information, comprising:
a hand held dental instrument;
a plurality of first gyroscope components each capable of generating an electrical output signal indicative of orientation of the respective first gyroscope component;
first mounting means for mechanically connecting said first gyroscope components to said dental instrument to provide electrical output signals indicative of the orientation of said dental instrument;
a plurality of second gyroscope components each capable of generating an electrical output signal indicative of orientation of the respective second gyroscope component;
second mounting means for mechanically connecting said second gyroscope components to a patient's jaw to provide electrical output signals indicative of the orientation of the jaw;
signal generation means for providing electrical output signals indicative of the translatory position of said dental instrument relative to said jaw;
third mounting means for mechanically connecting at least a part of said signal generation means to said jaw; and
computer means operatively connected to said first gyroscope components, said second gyroscope components and said signal generation means for receiving the electrical output signals thereof and for computing the position and orientation of said dental instrument relation to said jaw.

22. A method for use in a dental or medical application to operate on a patient, comprising the steps of:
attaching an articulated arm assembly to the patient's head;
automatically moving individual arms of said arm assembly to control position and orientation of an operating instrument attached to said assembly; and
automatically activating said instrument upon juxtaposition of an operating tip thereof with the patient.

23. The method defined in claim 22 wherein said step of attaching includes the steps of fastening a bite block to the patient's jaw and mounting said arm assembly to said bite block.

24. The method defined in claim 23 wherein said step of fastening includes the step of forming said bite block from stock elements.

25. A method for use in a dental or medical application to obtain three-dimensional structural information as to a patient, comprising the steps of:
attaching an articulated arm assembly to the patient's head;
manually moving a probe instrument attached to said arm assembly so that a tracer tip of said instrument contacts a surface of the patient;
automatically monitoring positions of individual arms of said arm assembly relative to each other during motion of said probe instrument; and
automatically calculating in digital form the traced surface of the patient.

26. The method defined in claim 25 wherein said step of attaching includes the steps of fastening a bite block to the patient's jaw and mounting said arm assembly to said bite block.

27. The method defined in claim 26 wherein said step of fastening includes the step of automatically machining at least one part of said bite block in accordance with electronic tooth surface data.

28. The method defined in claim 27 wherein said step of fastening further includes the step of automatically calculating an optimal point of attachment of said arm assembly to said bite block.

29. The method defined in claim 26 wherein said step of fastening includes the step of forming said bite block from stock elements.

30. The method defined in claim 26, further comprising the steps of automatically monitoring incremental motions between said bite block and the patient's jaw and automatically taking the incremental motions into account in calculating the traced surface of the patient.

31. The method defined in claim 25, further comprising the step of automatically moving said instrument in incremental motions about a point established during said step of manually moving.

32. The method defined in claim 31 wherein said step of automatically moving includes the step of attaching a drive device to said arm assembly so that said instrument is operatively connected to said drive device and energizing said drive device to move said instrument.

33. A device for use in operating on a patient, comprising:
an operating instrument having an operating tip;
mounting means for removably attaching said instrument to a patient;
linear drive means operatively connected to said instrument for automatically shifting said instrument in a given direction relative to the patient;
rotary drive means operatively connected to said instrument for automatically pivoting said instrument about an axis.

34. The device defined in claim 33 wherein said mounting means includes an articulated arm assembly and feedback means operatively coupled with said arm assembly for providing electrical signal feedback data as to positions of arm segments of said assembly relative to one another, thereby providing information as to the position of said instrument relative to the patient.

35. The device defined in claim 34, further comprising frame means for holding said instrument and locking means operatively connected to said articulated arm assembly for temporarily locking said arm segments relative to one another to thereby fix the location of said frame relative to the patient.

36. The device defined in claim 33 wherein said axis passes through said operating tip.

37. The device defined in claim 33 wherein said mounting means includes means for removably attaching said holder means and accordingly said instrument to a patient's jaw.

38. The device defined in claim 33, further comprising computing means operatively connected to said linear drive means and said rotary drive means for controlling said instrument to move according to a preprogrammed motion.

39. A device for use in operating on a patient, comprising:
an operating instrument;
a hand-held carrier, said instrument being movably connected to said carrier;
drive means mounted to said carrier and operatively connected to said instrument for moving same relative to said carrier;
tracking means operatively connected to said carrier for tracking position and orientation thereof relative to a patient; and
control means operatively connected said drive means and said tracking means for actuating said drive means to perform a predetermined operation on the patient partially in response to position and orientation of said carrier, as communicated to said control means by said tracking means.

40. The device defined in claim 39 wherein said tracking means includes an articulated arm assembly and feedback means operatively coupled with said arm assembly and to said computer for providing thereto electrical signal feedback data as to positions of arm segments of said assembly relative to one another, thereby providing information as to the position of said carrier and said instrument relative to the patient.

41. The device defined in claim 40, further comprising locking means operatively connected to said articulated arm assembly for temporarily locking said arm segments relative to one another to thereby fix the location of said carrier relative to the patient.

42. The device defined in claim 39 wherein said tracking means includes means for removably attaching said articulated arm assembly and accordingly said carrier and said instrument to a patient's jaw.

43. A method for use in providing a dental implant, comprising the steps of:
generating electrically encoded data specifying pre-existing bone structure in a patient's jaw;
transmitting said data to a computer;
operating said computer to predetermine an optimal position and an optimal orientation of an implant anchor; and
automatically providing an implant anchor in accordance with automatic determinations of said computer based on said data.

44. The method defined in claim 43 wherein said step of automatically providing includes the step of automatically manufacturing a mold and casting said implant anchor in said mold.

45. The method defined in claim 44 wherein said step of automatically manufacturing includes the step of automatically cutting a preform part in the form of said implant anchor and using said preform part to form said mold from refractory material.

46. The method defined in claim 43 wherein said step of automatically providing includes the step of selecting said implant anchor from a plurality of preformed anchors.

47. A device for use in a dental or medical application to track position and orientation of an instrument relative to a body part of a patient, comprising:
a reference element fixed to the body part of the patient;
a first articulated arm assembly connected to said reference element and to a stationary fixture, said first articulated arm assembly provided with first feedback means for providing electrical signal feedback data as to position of and orientation of said reference element relative to said stationary fixture; and
a second articulated arm assembly connected to said reference element and to the instrument, said second articulated arm assembly provided with second feedback means for providing electrical signal feedback data as to position of and orientation of said instrument relative to said reference element.

48. The device defined in claim 47, further comprising drive means mounted to said second articulated arm assembly and operatively connected to said instrument for automatically moving said instrument relative to said second articulated arm assembly.

49. The device defined in claim 48, further comprising locking means operatively connected to second articulated arm assembly for locking same to establish a fixed position for said drive means relative to said reference element.

50. The device defined in claim 48, further comprising locking means operatively connected to said reference element and to said drive means for fixing said drive means relative to said reference element.

51. The device defined in claim 47 wherein said body part is a person's jaw and said reference element is a bite block.

52. The device defined in claim 47, further comprising means for connecting said first feedback means and said second feedback means to a common computer.

53. A device for use in a dental or medical application to track position and orientation of an instrument relative to a body part of a patient, comprising:
 a reference element fixed to the body part of the patient;
 a first articulated arm assembly connected to said reference element and to a first stationary fixture, said first articulated arm assembly provided with first feedback means for providing electrical signal feedback data as to position of and orientation of said reference element relative to said first stationary fixture; and
 a second articulated arm assembly connected to a second stationary fixture and to the instrument, said second articulated arm assembly provided with second feedback means for providing electrical signal feedback data as to position of and orientation of said instrument relative to said second stationary fixture.

54. The device defined in claim 53, further comprising drive means mounted to said second articulated arm assembly and operatively connected to said instrument for automatically moving said instrument relative to said second articulated arm assembly.

55. The device defined in claim 54, further comprising locking means operatively connected to said second articulated arm assembly for locking same to establish a fixed position for said drive means relative to said second stationary fixture.

56. The device defined in claim 54, further comprising locking means operatively connected to said second stationary fixture and to said drive means for fixing said drive means relative to said second stationary fixture.

57. The device defined in claim 53 wherein said body part is a person's jaw and said reference element is a bite block.

58. The device defined in claim 53, further comprising means for connecting said first feedback means and said second feedback means to a common computer.

59. The device defined in claim 53 wherein said first stationary fixture and said second stationary fixture are the same fixture.

60. The device defined in claim 53 wherein said first stationary fixture and said second stationary fixture are spaced from one another.

61. A device for obtaining data as to position and orientation of a person's jaw, comprising:
 a multiplicity of arm segments;
 first mounting means for connecting said arm segments to one another to form an articulated assembly of said arm segments;
 second mounting means for fixing said articulared assembly to a stationary fixture;
 third mounting means for fixing said articulated assembly relative to a person's jaw; and
 feedback means operatively coupled with at least some of said arm segments for providing electrical signal feedback data as to positions of said arm segments relative to one another, thereby providing information as to the position of jaw relative to said stationary fixture.

62. A device for performing a surgical operation, comprising;
 a surgical instrument;
 first drive means operatively coupled to said instrument for incrementally moving said instrument about a point;
 second drive means operatively coupled to said instrument for shifting said point; and
 detector means operatively coupled to said instrument for monitoring position and orientation thereof.

63. The device defined in claim 62 wherein said detector means includes an articulated arm assembly and feedback means operatively coupled with at least some arm segments of said articulated arm assembly for providing electrical signal feedback data as to positions of said arm segments relative to one another, thereby providing information as to position and orientation of said instrument.

64. The device defined in claim 63 wherein said articulated arm assembly is linked to a patient on whom said instrument is actuated to operate.

65. The device defined in claim 63, further comprising locking means operatively connected to said articulated assembly for temporarily locking said arm segments relative to one another to thereby fix the location of said point.

66. The device defined in claim 62 wherein said second means includes an articulated arm assembly and motor means operatively coupled with at least some arm segments of said articulated arm assembly for driving said arm segments relative to one another, thereby shifting said point.

67. The device defined in claim 66 wherein said articulated arm assembly is linked to a stationary fixture.

68. The device defined in claim 66, further comprising an articulated linkage connecting said articulated arm assembly to said instrument, further comprising locking means operatively connected to said articulated linkage for temporarily locking individual links thereof relative to one another to firmly connect said articulated arm assembly to said instrument.

* * * * *

UNITED STATES PATENT AND TRADEMARK OFFICE
CERTIFICATE OF CORRECTION

PATENT NO. : 5,343,391

DATED : August 30, 1994

INVENTOR(S) : David R. Mushabac

It is certified that error appears in the above-indentified patent and that said Letters Patent is hereby corrected as shown below:

Delete Drawing Sheet 4 and substitute therefor the Drawing Sheet consisting of FIGS. 8-11, as shown on the attached page.

Signed and Sealed this

Twenty-first Day of March, 1995

Attest:

BRUCE LEHMAN

*Attesting Officer*    *Commissioner of Patents and Trademarks*